United States Patent
Veiner et al.

(10) Patent No.: US 7,854,892 B2
(45) Date of Patent: Dec. 21, 2010

(54) SPECIMEN-TRANSPORT MODULE

(75) Inventors: Craig R. Veiner, Miami, FL (US);
Frank M. Tappen, Plantation, FL (US);
Roberto Del Valle, Coral Gables, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/744,936

(22) Filed: May 7, 2007

(65) Prior Publication Data

US 2007/0207056 A1 Sep. 6, 2007

Related U.S. Application Data

(63) Continuation of application No. 10/794,702, filed on Mar. 5, 2004.

(51) Int. Cl.
*G01N 35/04* (2006.01)
(52) U.S. Cl. .............. 422/65; 422/63; 436/47; 436/48; 436/49; 198/465.1; 198/619
(58) Field of Classification Search .......... 422/63, 422/65; 198/465.1; 436/47, 48, 49
See application file for complete search history.

(56) References Cited

U.S. PATENT DOCUMENTS

| | | | |
|---|---|---|---|
| 3,897,216 A | 7/1975 | Jones | |
| 4,040,533 A | 8/1977 | De Boer et al. | |
| 4,454,939 A | 6/1984 | Kampf et al. | |
| 4,609,017 A * | 9/1986 | Coulter et al. | 141/1 |
| 5,008,082 A | 4/1991 | Shaw | |
| 5,207,986 A | 5/1993 | Kadota et al. | |
| 5,380,488 A | 1/1995 | Wakatake | |
| 5,687,849 A | 11/1997 | Borenstein et al. | |
| 5,720,377 A | 2/1998 | Lapeus et al. | |
| 5,735,387 A * | 4/1998 | Polaniec et al. | 198/690.1 |
| 5,861,563 A * | 1/1999 | Boyd et al. | 73/864.21 |
| 6,337,050 B1 | 1/2002 | Takahashi et al. | |
| 6,358,472 B1 * | 3/2002 | DeYoung et al. | 422/65 |
| 6,444,171 B1 | 9/2002 | Sakazume et al. | |
| 6,444,472 B1 | 9/2002 | Cohen et al. | |
| 6,521,183 B1 * | 2/2003 | Burri et al. | 422/65 |
| 6,571,934 B1 | 6/2003 | Thompson et al. | |

(Continued)

FOREIGN PATENT DOCUMENTS

EP 0478285 B1 2/1996

(Continued)

*Primary Examiner*—P. Kathryn Wright
(74) *Attorney, Agent, or Firm*—Warren W. Kurz; Mitchell E. Alter

(57) ABSTRACT

A specimen-transport module adapted for use with each of a plurality of specimen-processing instruments of a multi-instrument clinical workcell. Such module is adapted to transport individual racks of specimen-containers relative to a specimen-aspiration probe of an associated instrument in a workcell, as well as to transfer selected racks of specimen-containers to an adjacent and identical specimen-transport module associated with another clinical instrument of the workcell. Since the same transport system is used to both present specimens for aspiration and to transfer specimens between instruments, there is no need for two independent conveyances as is characteristic of the prior art. Preferably, the specimen-transport module includes a magnetic X/Y transport system that operates beneath a rack-supporting surface to advance racks in mutually perpendicular directions across a supporting surface via magnetic forces.

5 Claims, 18 Drawing Sheets

U.S. PATENT DOCUMENTS

| | | |
|---|---|---|
| 6,588,625 B2 | 7/2003 | Luoma, II et al. |
| 2002/0021983 A1* | 2/2002 | Comte et al. .................. 422/65 |
| 2002/0106814 A1* | 8/2002 | Matsubara et al. .......... 436/180 |
| 2006/0216199 A1* | 9/2006 | Koike .......................... 422/65 |

FOREIGN PATENT DOCUMENTS

| | | | |
|---|---|---|---|
| EP | 0871035 A2 | 10/1998 | |
| JP | 09196926 | * | 7/1997 |
| WO | 02090996 A2 | | 11/2002 |
| WO | 03093833 A1 | | 11/2003 |

* cited by examiner

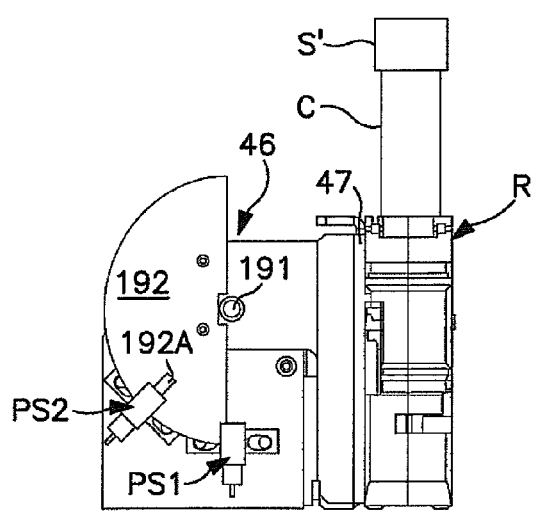 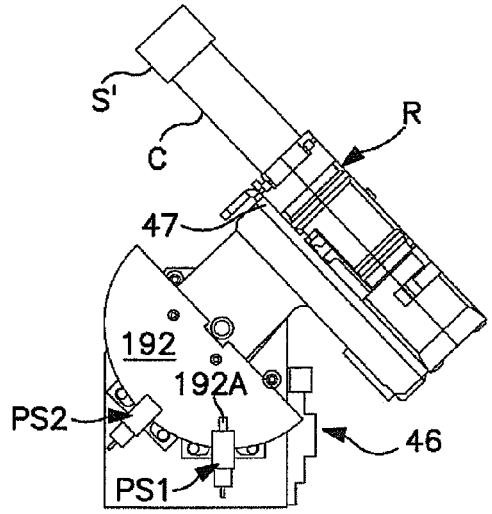
FIG. 16A  FIG. 16B
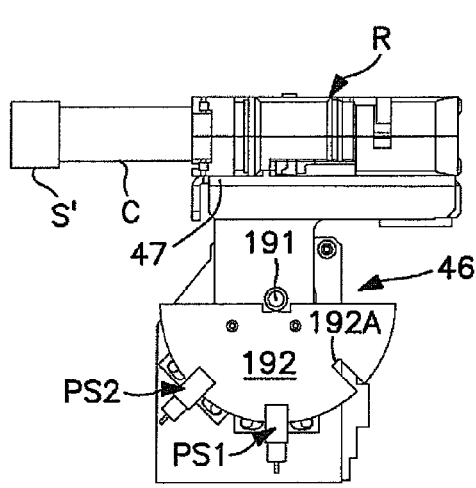 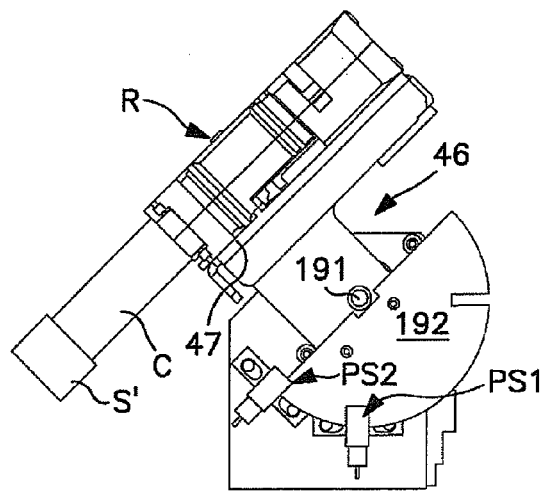
FIG. 16C  FIG. 16D

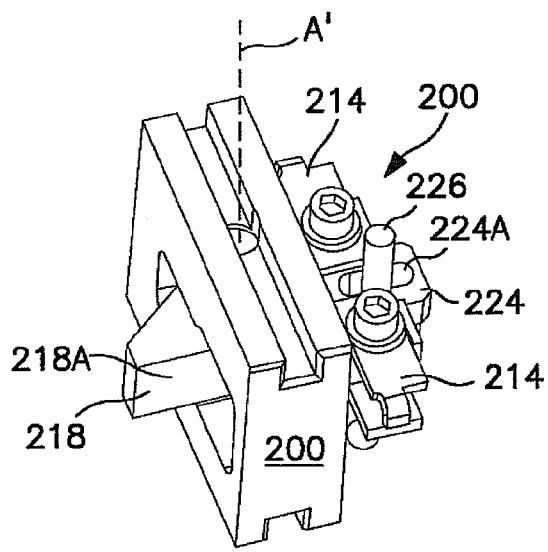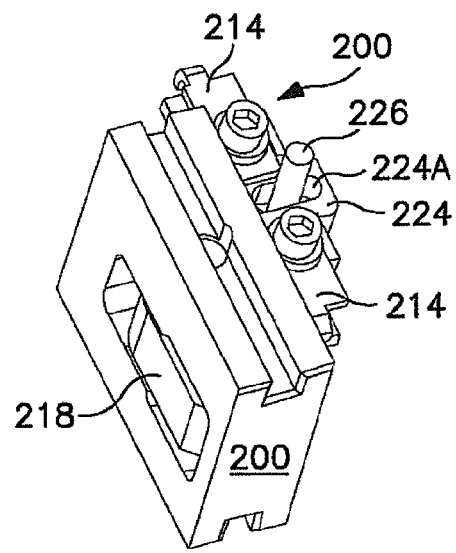
FIG. 18A  FIG. 18B
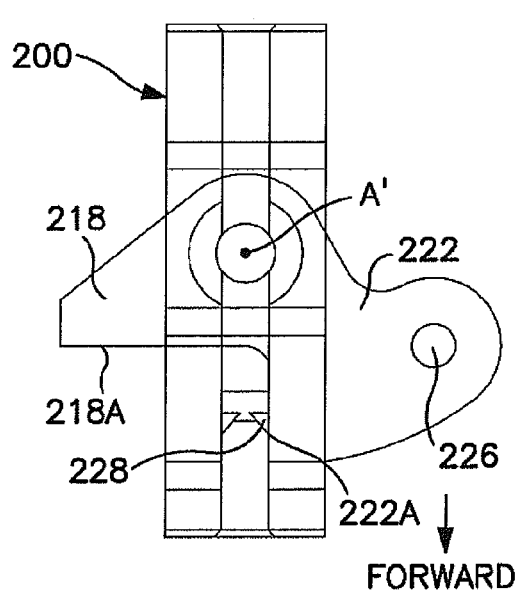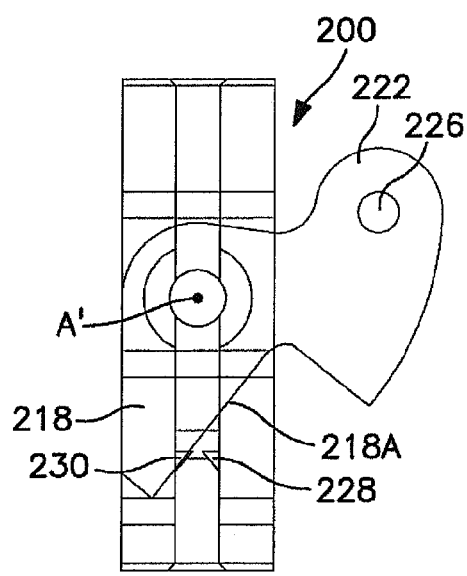
FIG. 19A  FIG. 19B

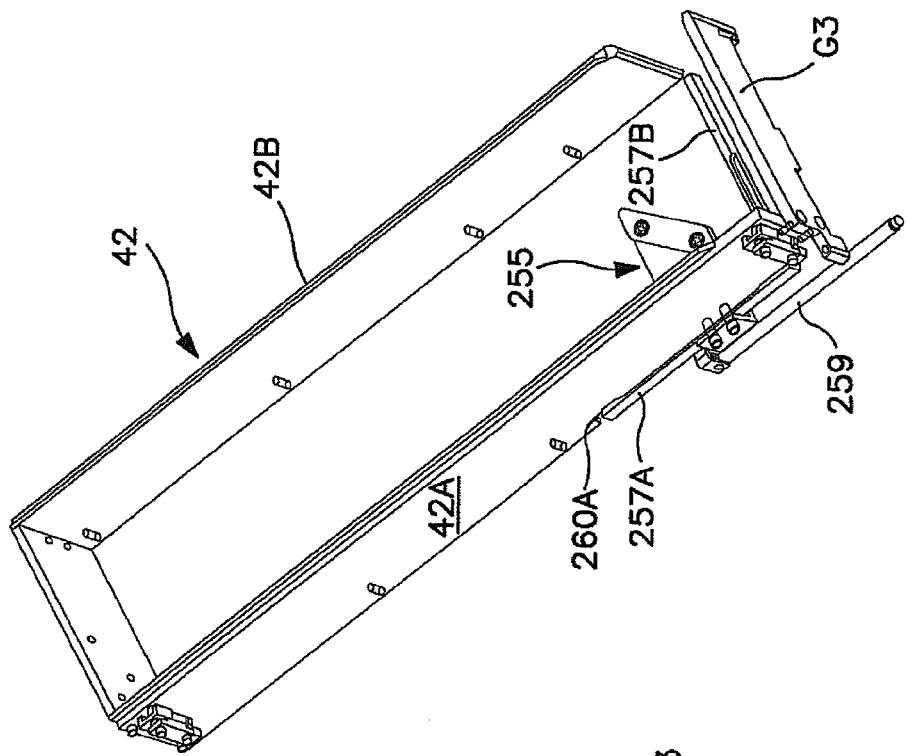
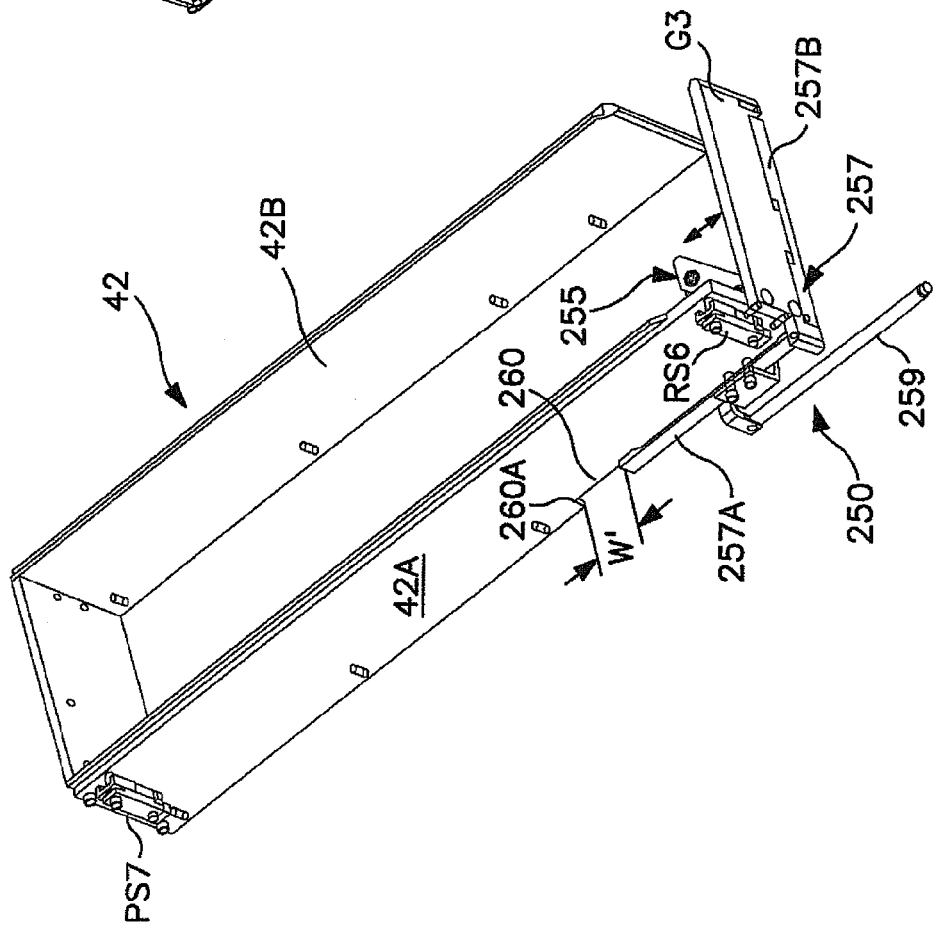

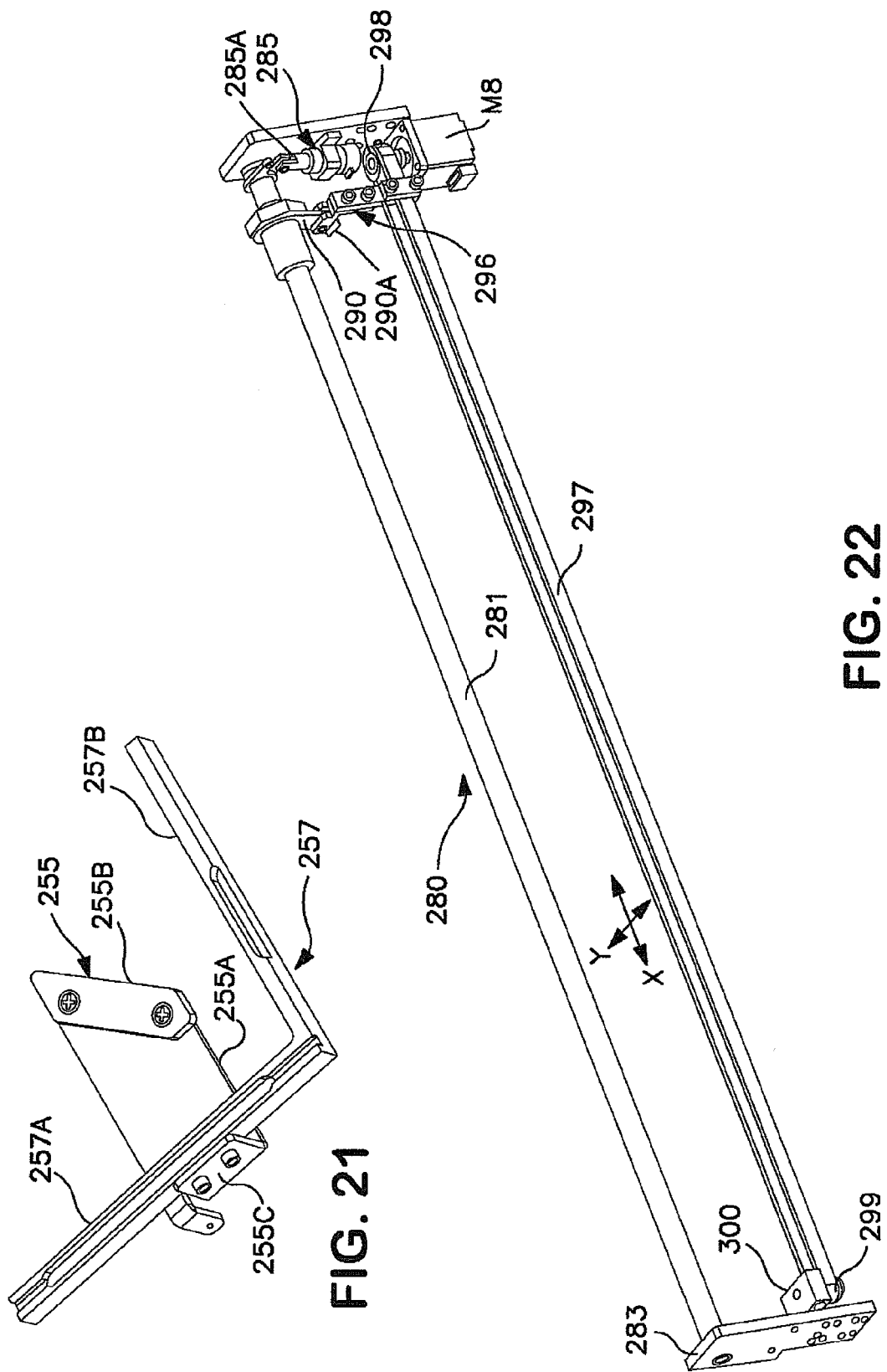

SPECIMEN-TRANSPORT MODULE

CROSS-REFERENCE TO RELATED APPLICATIONS

Reference is made to the following commonly assigned patent applications:

U.S. application Ser. No. 10/794,702, filed on Mar. 5, 2004, entitled "Specimen-Transport Module For A Multi-Instrument Clinical Workcell", from which this application is a continuation application, U.S. application Ser. No. 10/794,686 entitled "Magnetic Specimen-Transport System for Automated Clinical Instrument," now U.S. Pat. No. 7,028,831, and U.S. application Ser. No. 10/794,685 entitled "Specimen-Container Rack for Automated Clinical Instrument," now U.S. Pat. No. 7,331,474.

BACKGROUND OF THE INVENTION

1. Field of the Invention

The present invention relates to improvements in apparatus for transporting specimen-containers within an automated, multi-instrument clinical workcell. More particularly, this invention relates to a modular specimen-transport system that is adapted for use with each of a variety of different specimen-processing instruments of a clinical workcell, serving both to present specimen-containers to a specimen-aspiration probe of an individual instrument, and to transport specimen-containers between identical specimen-transport modules of adjacent instruments in the workcell.

2. The Prior Art

It is known in the art to perform diagnostic tests on various liquid biological specimens, e.g., whole blood, serum, urine, spinal fluids, etc., using different automated clinical instruments. In the analysis of whole blood specimens, for example, such automated instruments may include: (i) hematology instruments that operate to count and differentiate different blood cell types on the basis of their respective physical, electrical and/or light-scattering properties, and (ii) fluorescence flow cytometers that operate to differentiate different cell types by irradiating individual cells passing through an optical flow cell and detecting the fluorescence of certain fluorochromes to which the cells of interest have been conjugated or stained prior to analysis. Other automated instruments that may be used in a blood-analyzing workcell are specimen slide-makers that operate to automatically prepare optical slides of selected specimens for subsequent microscopic analysis. All of these instruments have in common a movably-mounted aspiration probe that is adapted to move vertically into a specimen-container for the purpose of aspirating a specimen for processing. While these different instruments can operate independently of each other, they are sometimes integrated or linked together to form a multi-instrument "workcell" in which a common system controller (typically microprocessor-controlled) serves to direct the operation of the individual instruments on a given specimen based on certain results to be achieved.

The biological specimens to be analyzed by clinical instruments are commonly collected in various types of sealed test tubes or containers, each usually having a puncturable cap through the above-noted aspiration probe of each instrument can enter and withdraw a desired aliquot of specimen for processing. Typically, five or six specimen tubes, each bearing encoded patient and test information in the form of a bar code, are supported for aspiration by a single rack or cassette. In a workcell environment, racks of specimen-containers are often transported between clinical instruments by a conveyor system. The latter operates to receive a rack of specimens at specimen-loading station spaced from the instruments and, as determined by the workcell's system controller, to selectively transport the rack to and from the different clinical instruments, depending on the test or processing to be conducted. Alternatively, the racks, or individual containers in a rack, may be transported to and from the different clinical instruments by a robotic arm. In either case, it will be appreciated that, if the inter-instrument conveyance fails, the workcell as a whole stops operating.

Most often, clinical instruments have their own integral specimen-transport system for receiving and advancing specimen-containers within the instrument. These sample-transport systems differ substantially in their mechanical make-up from instrument-to-instrument; as a result, they can be problematic in being integrated into a workcell architecture.

U.S. Pat. Nos. 6,444,472 and 5,720,377 disclose two different modular transport systems that are adapted for use with various clinical instruments to present racks of specimen-containers to a location at which a specimen can be aspirated or otherwise processed. Each of these rack-transport systems is a stand-alone unit comprising an input queue for receiving and aligning racks of specimen-containers to be processed; a cross-feed section to which the racks are moved in a direction perpendicular to the direction in which they are aligned in the input queue to present the containers for processing (e.g., aspiration of the contained specimens); and an output queue for receiving container racks in which the contained specimens have been processed. In the '472 patent, the rack transport module is used in combination with a robotic arm that operates to remove each individual specimen-container, one at a time, from a specimen rack located in the cross-feed section, and to transport the individual containers to one or more clinical instruments for processing. After specimen processing, the robotic arm is programmed to re-engage each specimen-container at the processing instrument, and to return it to an empty container-opening in a rack which is then advanced to the output queue. An elaborate and complex "walking beam" mechanism is used to physically lift each container rack above its supporting surface, and to advance the racks an incremental distance in the input and output queues, as well as in the cross-feed section. Thus, the specimen-container transport module of the '472 patent simply serves to advance racks of specimen-containers from an input queue to a location where the specimen-containers may be accessed by a robotic arm for processing. The module itself serves neither to present specimen-containers to an instrument for processing, nor to interface with other modules to transfer specimen-containers thereto.

In the above-noted '377 patent, the sample-transport module operates to convey racks of specimen-containers from an input queue to a location where the specimens may be aspirated from selected containers. The racks of containers are then discharged to an exit queue to await off-loading. A magnetic transport system is used to advance racks of specimen-containers along a linear path within the input queue from an input position, at which the racks are manually loaded, to a location at which each rack can be mechanically moved to a specimen aspiration station. Movement of the racks out of the input queue and into the specimen-aspiration position is effected by a conveyor belt with a series of outwardly-extending paddles. As the belt advances, the individual paddles engage the sides of the containers and thereby index the movement of the rack, one container at a time. Following specimen aspiration and testing, the specimen-container rack is mechanically urged out of the specimen-processing section by pusher mechanism that operates to engage an edge of the rack and to push the rack into the output queue. There, an indexing mechanism advances the racks to an off-loading position. While the specimen-transport module of the '377 patent may be useful in presenting specimen-containers to different clinical instruments, e.g., those used in a multi-instrument workcell, there is no discussion in this patent regarding how one might transfer specimen-container racks from one module to another, as would be necessary to link the clinical instruments of a fully automated workcell. Presumably, one would use a robotic arm or some other independent conveyor system to provide this function. Obviously, such an approach would add considerable cost and complexity to the workcell.

SUMMARY OF THE INVENTION

In view of the foregoing discussion, an object of this invention is to provide a modular specimen-transport apparatus that is capable of satisfying not only the specimen presentation needs of an individual clinical instrument with which it is directly associated, but also the specimen transport needs of a multi-instrument workcell in which specimens must be transferred between individual instruments of the workcell for testing and/or processing.

Another object of this invention is to provide a specimen-transport module that eliminates the need for robotic arms and other independent specimen-transport conveyances for transporting specimen-containers between adjacent instruments of a multi-instrument clinical workcell.

According to a first aspect of the invention, there is provided a specimen-transport module that is adapted for use with each of a plurality of specimen-processing instruments of a multi-instrument clinical workcell. Such module comprises a housing defining (i) an input buffer for receiving and supporting a plurality of racks of specimen-containers, (ii) a specimen-aspiration station for supporting a rack of specimen-containers in a position to be accessed by an aspiration probe of an associated specimen-processing instrument, (iii) an output buffer for supporting a plurality of racks in a position to be removed from the module, and (iv) a rack-transfer station for supporting individual racks of specimen-containers at a location to be transferred to a corresponding rack-transfer station of an adjacent and identical specimen-transport module associated with another specimen-processing instrument. The specimen-transport module of the invention further includes a specimen-transport system for transporting individual specimen-container racks among the above-noted buffers and stations of the module housing. According to a particularly preferred embodiment, the specimen-transport system comprises an X/Y magnetic transport system that interacts with the racks via magnetic forces to selectively transport the racks in mutually perpendicular directions within the module housing. Also preferred is that the module housing further defines a specimen-processing station at which the racks of specimens can be processed, e.g., repeatedly inverted to homogeneously mix the specimens, prior to specimen-aspiration by an instrument directly associated with the module.

In accordance with a second aspect of the invention, a modular, multi-instrument clinical workcell is provided. Such a workcell comprises: (i) at least two clinical instruments adapted to process liquid biological specimens presented to an aspiration probe associated with each instrument, and (ii) a like number of identical and adjacent specimen-transport modules, one being operatively associated with each of the clinical instruments. In accordance the invention, each of the specimen-transport modules comprises an X/Y-movable specimen-transport system that functions both to (a) transport individual racks of specimen-containers to a position in which the specimen-aspiration probe of an associated instrument can access and aspirate specimens from the specimen-containers, and (b) transport individual racks of specimen-containers to a position in which the transported rack can be acted upon and further transported by the X/Y-movable specimen-transport system of the adjacent specimen-transport module.

Thus, by using the same specimen-transport system to perform both functions, i.e., to present specimens for aspiration, and to transfer specimens from one instrument to another, the prior art's need for two independent conveyances to perform these tasks is obviated, and a simpler and more reliable workcell results. It will be appreciated that the specimen-transport module of the invention is not only complete in its functionality with regard to the specimen-presentation needs of any individual clinical instrument of the workcell operating alone, but also it is capable of transferring and receiving specimen-containers to and from adjacent identical specimen-transport modules, whereby multiple specimen-transport modules act collectively as a specimen transport system for the workcell.

According to a third aspect of the invention, a specimen-transport module of the type described herein is provided with multiple independent specimen rack-transport mechanisms for transporting racks of specimen-containers between adjacent modules of a multi-instrument clinical workcell. Thus, according to another preferred embodiment of the invention, a redundant rack-transport mechanism, independent of the primary rack-transport mechanism noted above, is provided for transporting individual racks of specimen-containers between first and second rack-transfer stations of the module, whereby an individual specimen-transport module may be by-passed, as may be required in the event of a failure of the primary transport system or its associated clinical instrument, allowing the workcell to continue to function notwithstanding such failure.

According to a fourth aspect of this invention, there is provided a new and improved apparatus for simultaneously mixing a plurality of biological specimens, each being contained by one of a plurality of specimen-containers supported by specimen-container rack. Such apparatus includes a movably-mounted rack-engaging member for releasably engaging a specimen-container rack moved into contact therewith, and means for providing a reciprocating movement of the rack-engaging member along an arcuate path of sufficient length to repeatedly invert and re-invert the specimen containers of an engaged rack, whereby the contained specimens are thoroughly mixed. Preferably, a tongue-in-groove type engagement is made between the movably-mounted rack-engaging member of the mixing apparatus and a specimen container rack to provide a secure engagement between these elements, and a magnetic member is used to exert a force between the rack-engaging member and the specimen-container rack that overcomes any vibrational or other force that would tend to disengaging the rack-engaging member and an engaged rack during the specimen mixing operation.

According to fifth aspect of this invention, an input buffer of a specimen-transport module of the type described herein is provided with a cam-actuated pusher mechanism which operates to advance a stack of specimen-container racks along an input queue towards an exit position in the buffer. Preferably, the pusher mechanism comprises a pair of movably-mounted pusher fingers that are caused to extend into the buffer when a force is exerted on the fingers tending to advance the fingers towards the front of the buffer, and to retract from the buffer when a force is exerted on the fingers in the opposite direction.

According to yet another aspect of the invention, an output buffer of a specimen-transport module of the type described herein comprises a movably-mounted rack-pushing member that is adapted to push a processed rack from a loading position towards an off-loading position at the end of the output buffer. Preferably the driving force of such member is provided by the same X/Y movable truck used to transport specimen-container racks throughout the specimen-processing portion of the specimen-transport module. Preferably, a processed rack is pushed into the output buffer only by a distance slightly greater than the width of a rack, allowing the X/Y movable truck to retrieve the last specimen-container rack in an output queue of such racks, e.g., to perform repeat or reflex testing on a specimen of interest, using the same rack-transporting scheme (e.g., magnetic forces) used to transport the racks within the specimen-processing portion of the module. Each time a rack is pushed into the output queue, it is done so with a force sufficient to advance the entire output queue towards the off-loading position of the output buffer.

The invention and its various aspects and advantages will be better understood from the ensuing detailed description of preferred embodiments, reference being made to the accompanying drawings in which like reference characters denote like parts or components.

BRIEF DESCRIPTION OF THE DRAWINGS

FIGS. 16A-16D are side illustrations of the specimen-mixing device of FIGS. 15A and 15B showing the position of a specimen container rack at four different times during a specimen-mixing operation;

FIGS. 18A and 18B are enlarged perspective illustrations of a preferred cam-actuated pusher device comprising the FIGS. 17A and 17B apparatus;

FIGS. 19A and 19B illustrate the cam member used in the apparatus of FIGS. 19A and 19B;

FIGS. 20A and 20B are perspective illustrations of a preferred mechanism for advancing specimen-container racks in the output buffer portion of the specimen-transport module of the invention;

FIG. 21 is an enlarged perspective view of a portion of the apparatus shown in FIGS. 20A and 20B; and FIGS. 22 and 23 illustrate a preferred redundant drive mechanism for advancing specimen-container racks between adjacent specimen-transport modules.

DETAILED DESCRIPTION OF PREFERRED EMBODIMENTS

Figure 1:
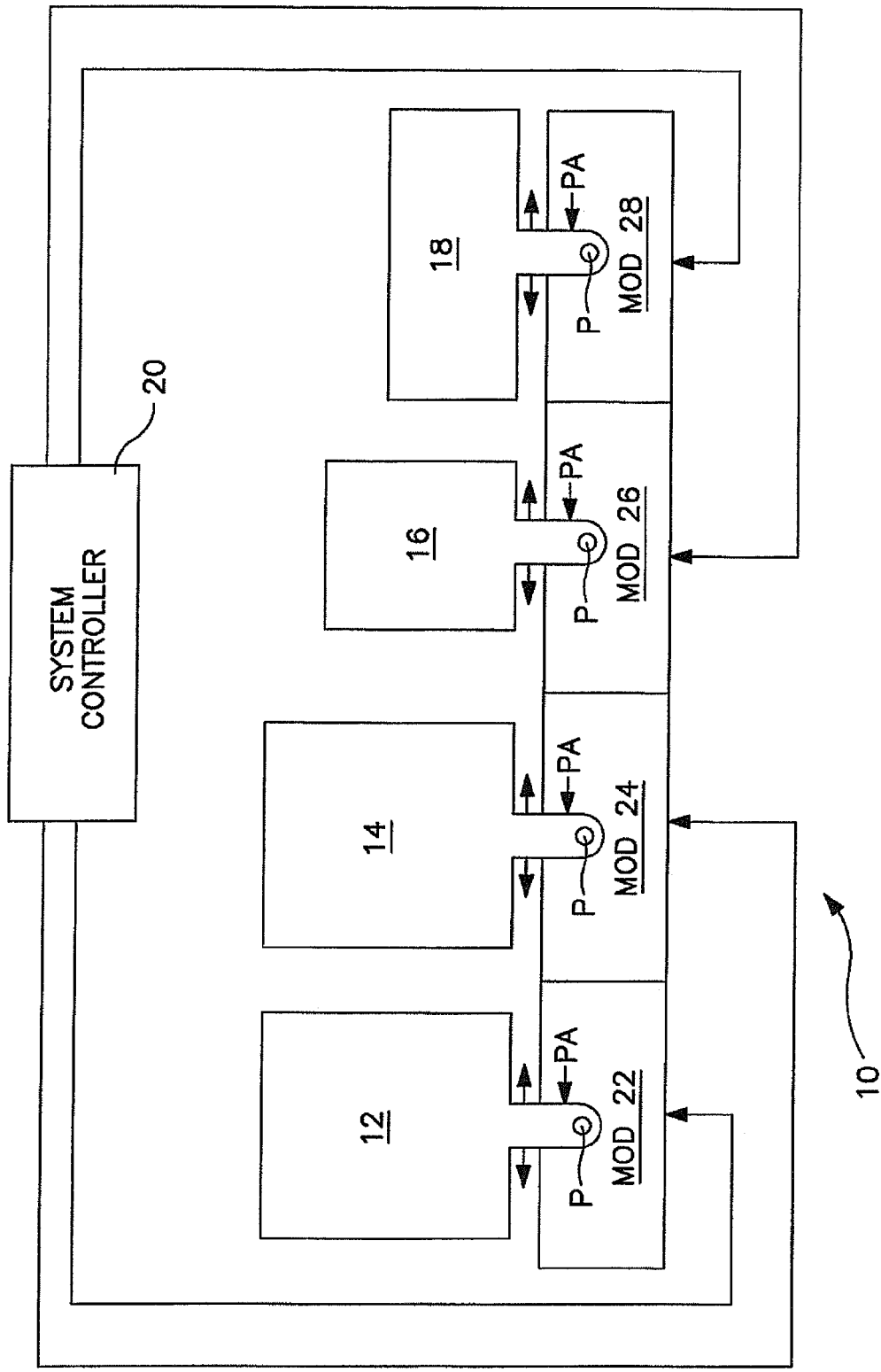
FIG. 1 is a schematic illustration of a multi-instrument clinical workcell embodying the present invention.

Referring now to the drawings, FIG. 1 schematically illustrates a multi-instrument workcell 10 that is adapted to analyze and/or otherwise process a whole blood specimen presented to it. Each of such specimens is contained by a test tube or other container C that is supported, together with additional containers, in a generally upright orientation and in a linear array, by a specimen-container rack of the type best illustrated in FIG. 10. In the embodiment shown in FIG. 1, workcell 10 comprises four separate clinical instruments 12, 14, 16 and 18, that operate under the control of a common, microprocessor-based, system controller 20. Instruments 12 and 14 may be, for example, hematology instruments that operate, in a conventional manner, to differentiate and count the constituent blood cells of the whole blood specimen on the basis of DC volume, RF-conductivity and/or light scatter measurements made on each cell as it passes through the sensing aperture of a conventional flow cell. Instrument 16 may be, for example, a fluorescence flow cytometer that operates, in a conventional manner, to differentiate cell types based on the combination of fluorescence measurements and either light-scatter, DC volume or RF conductivity measurements made on each cell as it is made to pass through the sensing zone of an optical flow cell. Instrument 18 may be, for example, a slide-maker/slide-stainer device that produces and subsequently stains a smear of specimen on a microscope slide that can be subsequently analyzed under a microscope. While these clinical instruments may substantially differ in the tasks they perform and, to a large extent, their mechanical make-up, each instrument has in common a movably-mounted aspiration probe assembly PA that is movable both vertically (into the plane of the drawing) so as to enter a specimen-container in order to aspirate a small volume of the contained specimen for processing, and laterally (as indicated by the arrows) so as to enter any one of the specimen-containers supported by a specimen-container rack.

In accordance with the present invention, workcell 10 further comprises a plurality of identical specimen-transporting modules (MOD 22, MOD 24, MOD 26 and MOD 28), one being operatively connected to, or otherwise associated with, each of the four clinical instruments 12, 14, 16 and 18. Each of the specimen-transporting modules provides at least two functions: Firstly, it functions to satisfy all specimen-presentation needs of the instrument with which it is directly associated, i.e., it functions to (i) receive multiple racks of specimen containers manually delivered to an input buffer of the module, (ii) selectively transport such racks from the input buffer to a specimen-aspiration station in which all of the specimen containers of given rack are accessible to the aspiration probe of the associated instrument, and (iii) deliver a rack to an output buffer following a desired specimen aspiration from all or selected ones of the containers in the rack. Upon being delivered to the output buffer, a rack, may be advanced to an off-loading position where it can be manually removed from the module or, alternatively, it may be returned to the specimen-aspiration station for reflex or repeat testing, as may be the case if a first test result indicates that a second aspiration of a given sample is required, or if a first test result is clearly erroneous. Secondly, the specimen-transporting module of the invention functions to transfer racks of specimen-containers between adjacent instruments, thereby enabling all instruments of the workcell to process a given specimen without need for any independent specimen-transfer mechanism, e.g., a robotic arm, or a conveyor system. To provide the latter function, each of the modules is rigidly connected to adjacent modules, allowing the modules to pass specimens back and forth, as described below with particular reference to FIG. 6. Preferably, each of the specimen-transport modules of the invention provides a third function, namely, that of preparing a specimen for subsequent processing. Such sample-preparation preferably comprises the step of mixing the contents of a specimen-container immediately prior to being aspirated by its associated instrument for processing. Such mixing is achieved by repeatedly inverting a specimen-container rack and the multiple containers it holds. The structural details of a preferred specimen-mixing station are described below with reference to FIGS. 15A and 15B.

Figure 2:
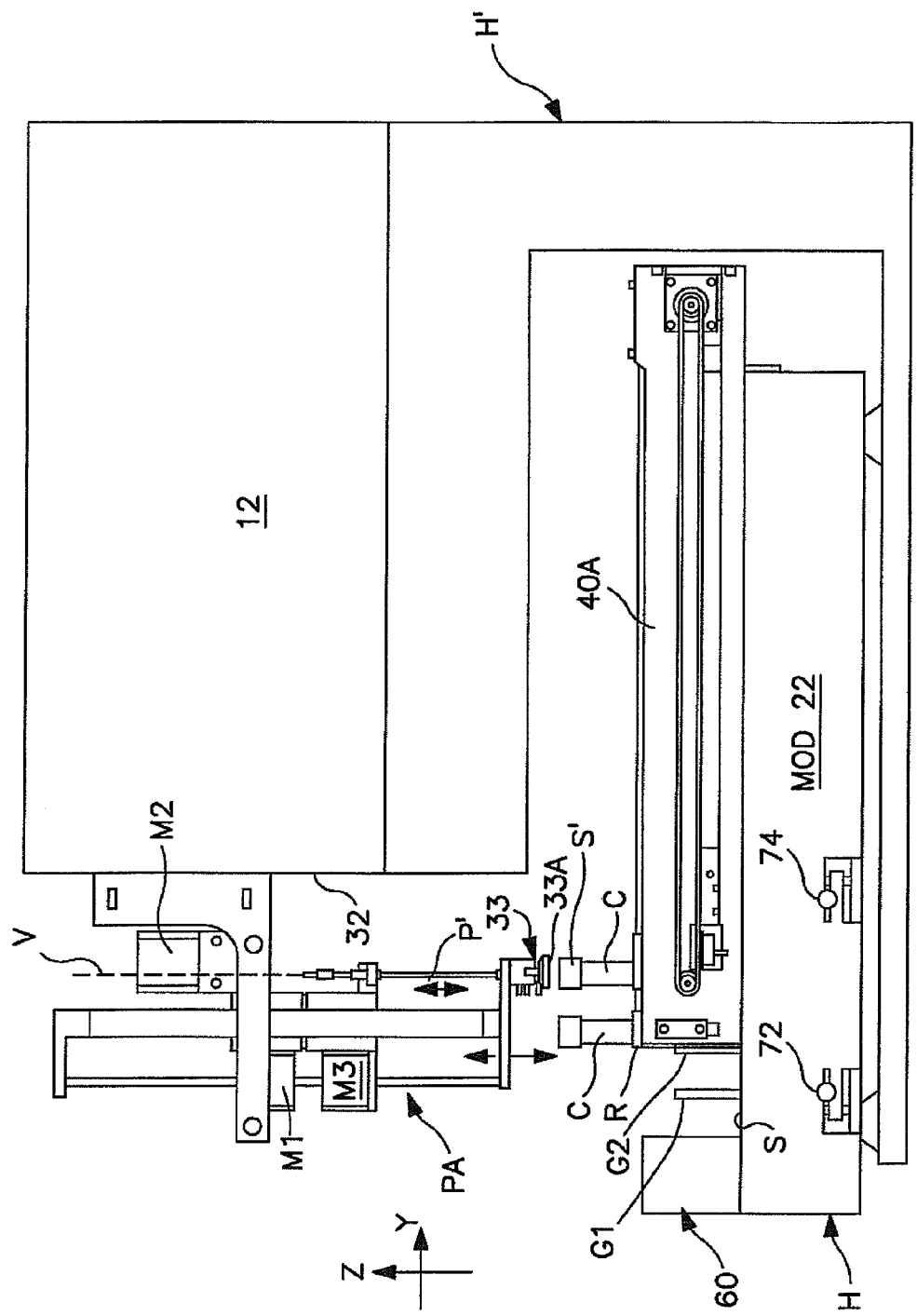
FIG. 2 is a side illustration of a preferred specimen-transport module shown in combination with a clinical instrument.

In the side illustration of FIG. 2, the relationship between a specimen-transport module, e.g., MOD 22, and its associated clinical instrument, in this case instrument 12, is shown. To minimize the space requirements of the module/instrument combination, the instrument is designed to enable a major portion of the module housing H to underlie the main housing H' of the clinical instrument. The instrument's aspiration probe assembly PA extends forwardly of the front wall 32 of the instrument housing, and the specimen-transport module operates to selectively support a specimen-container rack R in an aspiration position 50 (shown in FIG. 3) so that the specimen-containers C supported by the rack are arranged in a common vertical plane V that coincides with the plane of vertical movement of the aspiration probe P. The structural and operational details of the probe assembly are well understood and form no part of the invention. Briefly, however, movement of the probe assembly is controlled by three stepper motors, M1, M2 and M3, that operate under the control of the system controller 20. Stepper motor M1 operates to move the aspiration probe and a stripper mechanism 33 in a vertical plane, i.e., along the Z coordinate in FIG. 2, whereby the bottom surface 33A of the stripper mechanism can be moved downwardly into contact with the top surface of a rubber seal S' that encloses the top of the specimen container containing the sample to be aspirated. Stepper motor M3 then operates to control the vertical position of the aspiration probe P of the probe assembly, whereby the probe tip can be driven downwardly so as to puncture the seal S' and enter the container for the purpose of aspirating a volume of specimen from within the container. Following specimen aspiration, motor M3 then operates to raise the aspiration probe out of the container. As the probe moves upwardly, the stripper mechanism 33 is held stationary and in contact with the seal S', thereby resisting the tendency of the upwardly-moving aspiration probe to lift the container out of the rack as a result of the frictional forces between the container seal and the aspiration probe. After the probe tip clears the top of the container seal, motor M1 operates to lift both the stripper mechanism and the aspiration probe to a vertical position in which the stripper mechanism is well clear of the container seal. The third stepper motor M2 operates to selectively advance the probe assembly laterally, i.e., in a horizontal plane, whereby the aspiration probe may access any one of the specimen containers supported by a rack located at an specimen-aspiration station 50, shown in FIG. 3.

Figure 3:
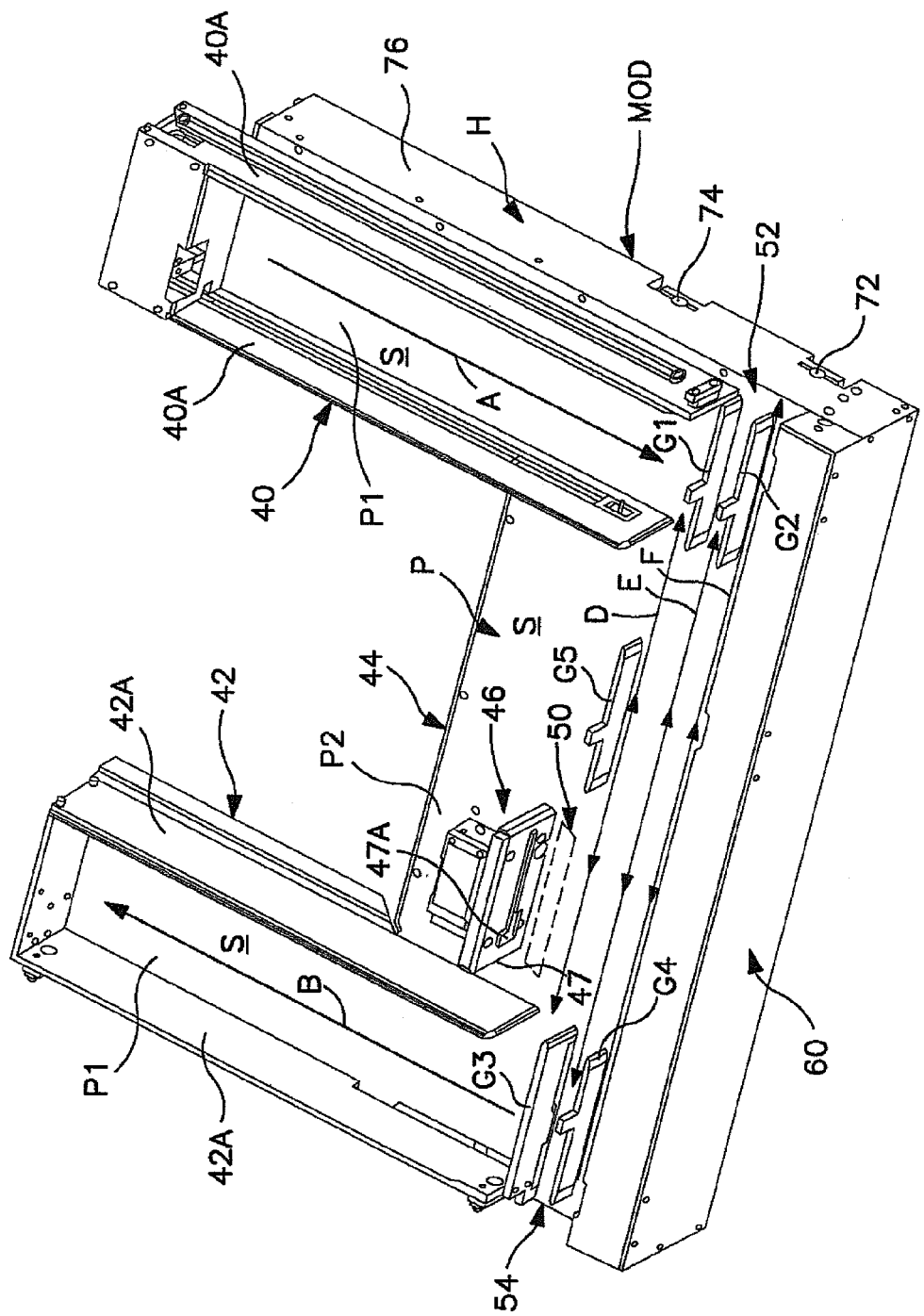
FIG. 3 is a perspective illustration of a preferred specimen-transport module embodied by the present invention.
Figure 4:
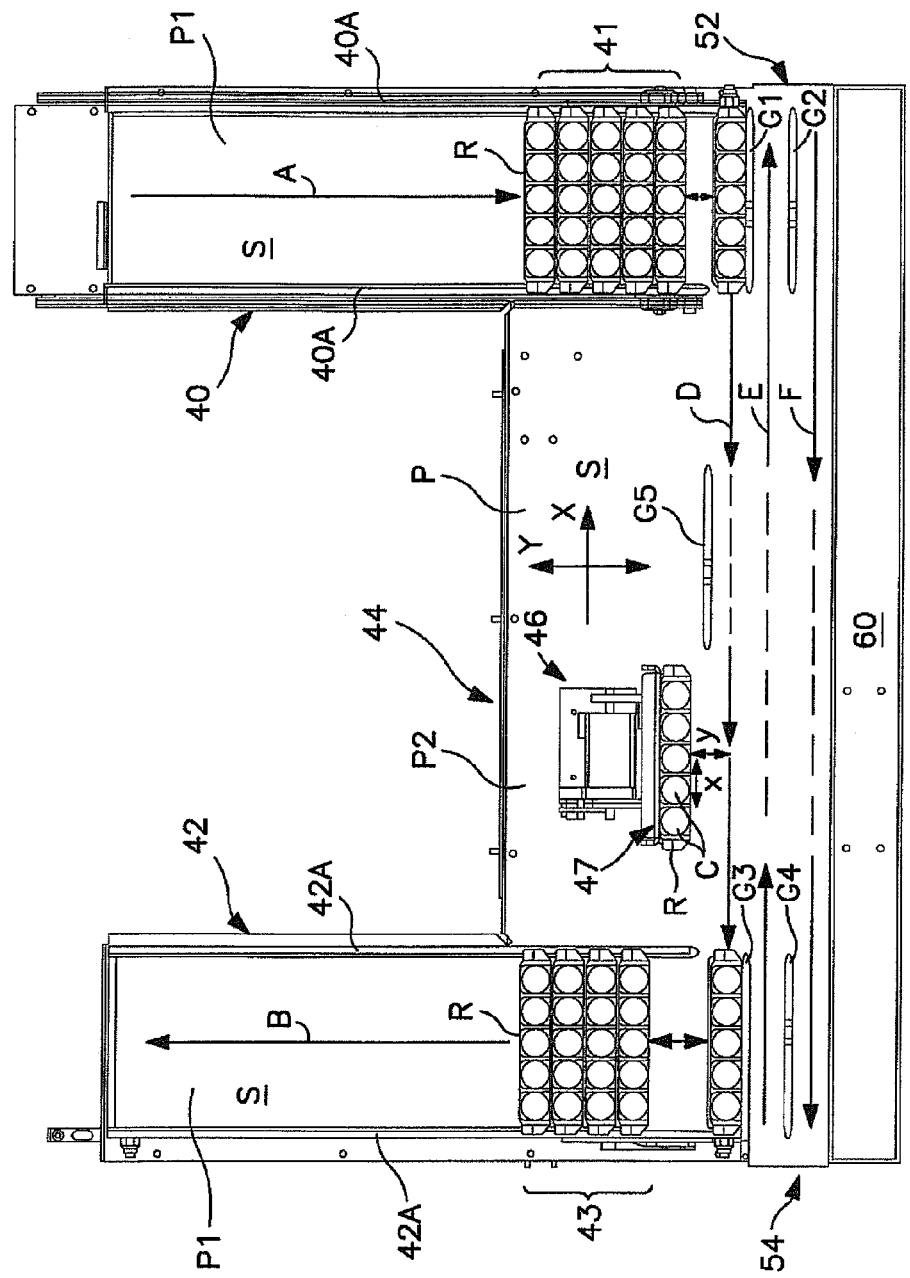
FIGS. 4 and 5 are top and front views, respectively, of the apparatus shown in FIG. 3, further illustrating the lateral positions of various specimen-container racks transported by such apparatus.
Figure 5:
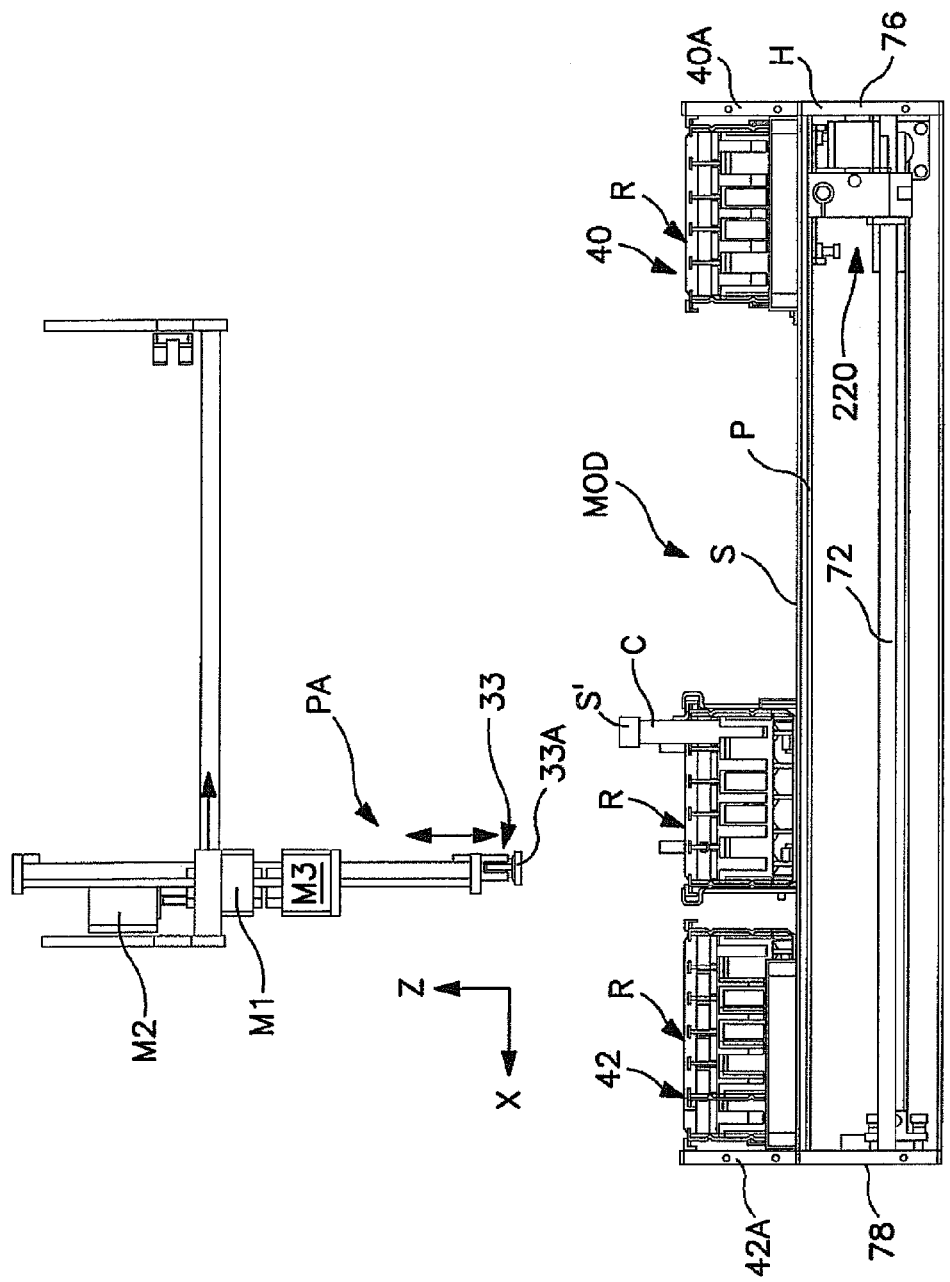
Figure 11A:
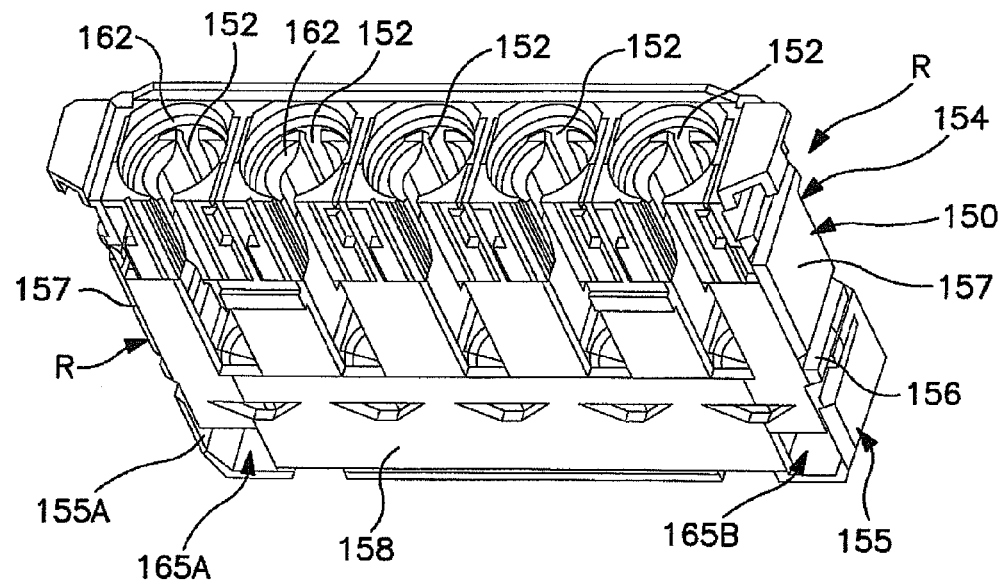
FIGS. 11A and 11B are top-front side and bottom-rear side perspective views, respectively, of a preferred specimen-container rack adapted for use in the specimen-transport module of the invention.
Figure 11B:
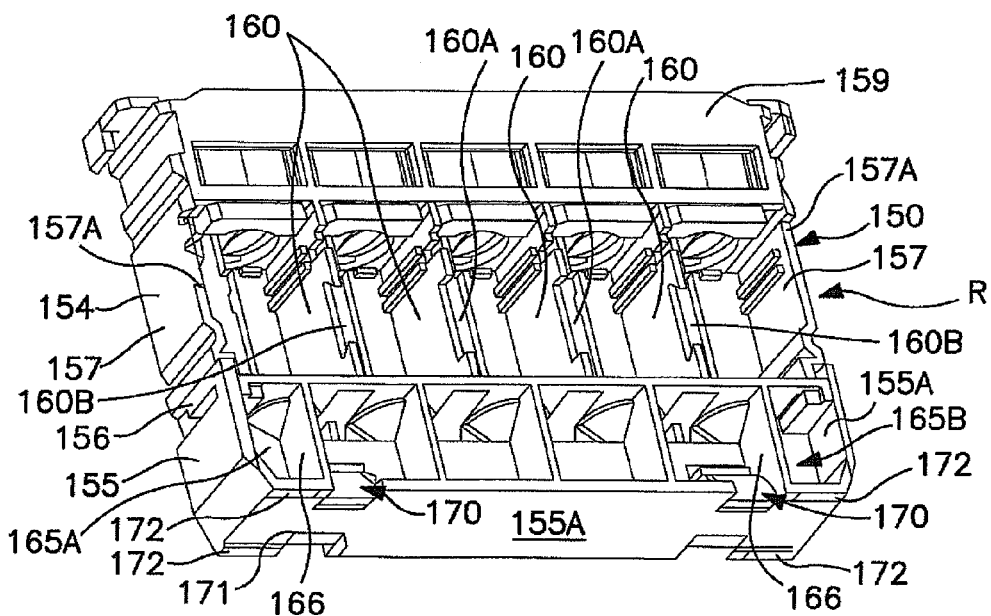

Referring additionally to FIGS. 3 and 4, a preferred structure for the specimen-transport module of the invention comprises a housing H that defines (i) an input buffer 40 that is adapted to receive and support up to, say, twenty of the specimen-container racks R of the type shown in FIGS. 11A and 11B; (ii) a specimen-processing section 44 through which individual racks of specimen-containers are advanced and presented to the aspiration probe assembly of an associated clinical instrument for specimen aspiration and processing; and (iii) an output buffer 42 in which racks of specimen-containers are accumulated after their respective specimens have been processed. Whereas each of the input and output buffers defines but a single path, respectively indicated by arrows A and B in FIG. 3, along which the specimen-container racks can travel on their way towards and away from the specimen-processing section 44, the racks may travel along any of three different paths, indicated by the arrows D, E and F in FIG. 3, while passing through the processing section. Normally, in processing the specimen-containers of a given rack, the rack is conveyed along the specimen-processing path D, where it passes a specimen-mixing station 46 and the afore-noted specimen-aspiration station 50. While positioned at the specimen-aspiration station 50, a movably-mounted specimen-mixing plate 47 acts, as described below, to lift and repeatedly invert a specimen-container rack located in position 50, whereby the contents of the containers in the rack are thoroughly mixed prior to the specimen-aspiration process. If and when it is necessary to transfer a specimen rack to another instrument for processing, the rack is advanced along either of paths E or F, whereby the rack can be positioned at either of two rack-transfer stations 52, 54 located at the opposing lateral edges of the module housing H. At the front of housing H, i.e., adjacent path F of the module, an elongated housing 60 is provided that extends along the entire width of the module. As described below with reference to FIGS. 22 and 23, housing 60 contains a redundant drive mechanism that operates to transport specimen-container racks in either direction along path F of the specimen-transport module, whereby racks can be passed through, and thereby by-pass, a module in which the primary rack-transport mechanism, described below, is either busy or, for some reason, not operating.

As best shown in FIGS. 3 and 4, module housing H comprises a U-shaped top plate P with the opposing legs P1 of the plate serving as the rack-supporting surface S of the input and output buffers 40 and 42, and the base portion P2 of the plate serving as the surface S on which the racks are supported in the processing section 44. Surface S of the plate P is smooth, plane and featureless, and it is this surface that supports the bottom surface of the specimen-container racks as they are moved throughout the confines of the module. Preferably, plate P is a non-magnetic stainless steel plate about 1.5 mm. in thickness. Each of the input and output buffers 40 and 42 comprises a pair of parallel lateral walls 40A, 40B; and 42A, 42B, respectively. These walls extend upwardly from surface S and are spaced apart by a distance slightly greater than the length L of the specimen-container racks, whereby the rack may be received by the buffers and aligned as shown in FIG. 4. Two pair of upwardly-extending and parallel guides members, G1, G2, and G3, G4, are arranged on surface S at the rack-transfer stations 52 and 54 to assure that the racks are properly aligned (i.e., not skewed) on paths E and F during the transfer of racks between modules. Guide G1 further serves as a stop against which racks in the input buffer can be registered prior to being moved edgewise into the specimen-processing section of the module. A fifth guide member G5 serves to properly align each rack as it approaches the specimen-aspiration station 50.

In the top view of FIG. 4, the movement of individual specimen-container racks R within a specimen-transport module is best illustrated. Individual racks are manually loaded at a loading station within the input buffer 40, typically to the rear of the last rack in the input queue 41, i.e., the rack farthest from the front housing 60. The racks are mechanically urged toward the front housing 60 and nearly into engagement with guide member G1 by a cam-actuated pusher mechanism, described below with reference to FIGS. 17A and 17B, and FIGS. 18A and 18B. Upon contacting guide member G1, a rack is registered for edgewise transport through the specimen-processing station 44 of the module. Such transport is preferably effected by a magnetic X/Y drive mechanism 70, shown in FIG. 7 and described below, that underlies surface S. Drive mechanism 70 operates to first advance a rack along path D (i.e., along the X coordinate) to a position opposite, but spaced from, the mixing device 46. Next, as shown in FIG. 4, the rack is moved in the Y direction by a distance y (about 40 mm) and into contact with a rack-engaging plate 47 of the mixing device 46. Next, the rack is advanced a short distance x (about 12 mm.) in the X direction, thereby providing positive engagement between the rack and plate (via an arrangement of a tongue 47A carried by mixing plate 47, and groove (notches 160B) carried by the rack, described below with reference to FIGS. 13 and 14). At this point, the specimen-containers in the rack are in position to have their respective contents mixed and aspirated. As discussed below, multiple specimens (i.e., corresponding to the number of containers in the rack) are mixed simultaneously and repeatedly. Between certain successive mixings, as explained below, the specimen from a selected container is aspirated by the probe assembly PA. Mixing is effected by rotating the mixing plate 47 and a rack attached thereto, as shown in FIGS. 16A-16C, thereby temporarily inverting the specimen-containers. After all specimens have been mixed and aspirated for processing, the rack is moved backwards by a distance x, along the X axis, to disengage the rack from the mixing device, and the rack is moved forwardly by a distance y along the Y axis (i.e., towards housing 60) until it reaches path D. Thereafter, the rack can be moved in the X direction and into the output queue 43 within output buffer 42, where a pushing device (described below with reference to FIGS. 20A and 20B) operates to advance a stack of racks along path B towards an off-loading station where the racks can be manually removed from the module. Alternatively, a processed rack can be moved to either of paths E or F, where the rack can be advanced to either of the two rack-transfer stations, 52, 54, so that it may be received and transported by an adjacent module, and processed by an adjacent instrument. Or, a rack can be transported back to the aspiration station, e.g., for reflex testing.

Figure 6:
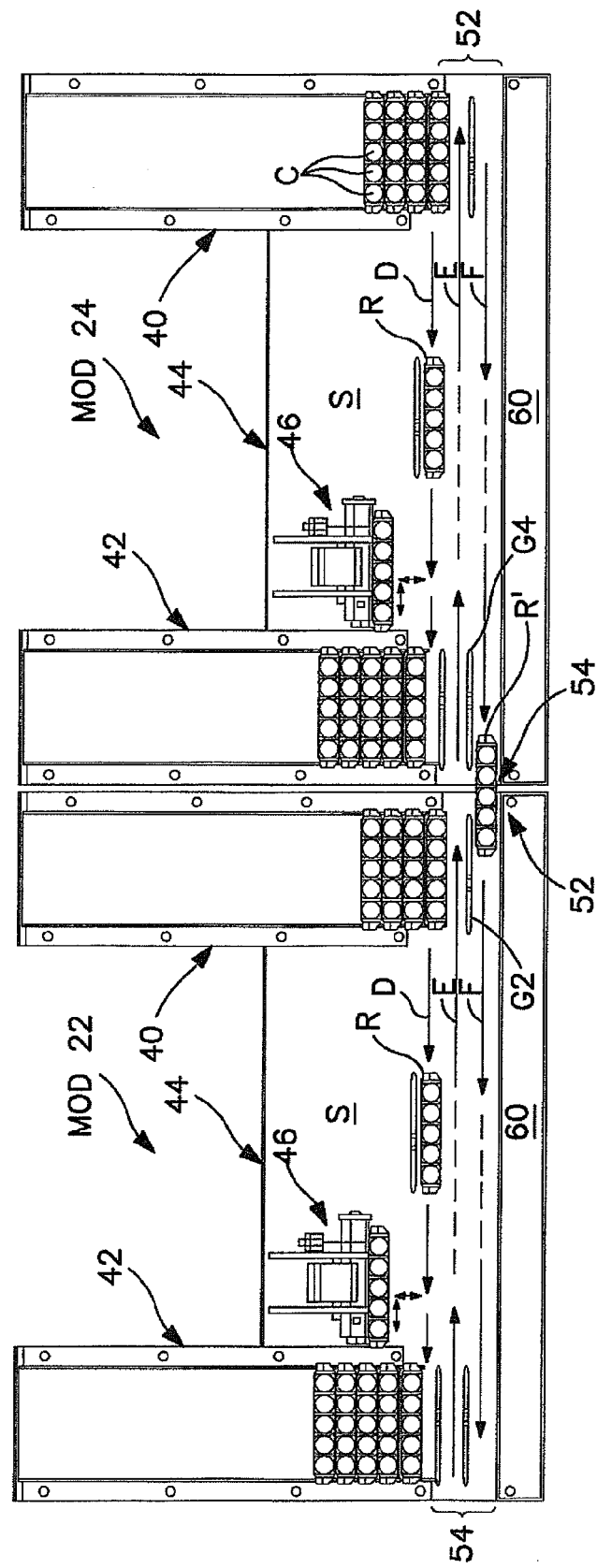
FIG. 6 is a top plan view of two adjacent specimen-transport modules of a multi-instrument workcell illustrating the transfer of a specimen-container rack from one module to another.

Referring to FIG. 6, two adjacent specimen transport modules, MOD 22 and MOD 24, are depicted during the process of transferring a specimen-container rack R' from MOD 24 to MOD 22. Here, as is apparent, the system for transporting specimen-container racks in MOD 22 is external to the system for transporting specimen-container racks in MOD24. As shown, rack R' has been transported along path F from the rack-transfer station 54 of MOD 24 to the corresponding path F of rack-transfer station 52 of MOD 22. As explained below, rack R' has been advanced to the position shown by an X/Y magnetic drive system 70 of MOD 24. In this position only one-half of the rack remains on surface S of MOD 24, and the remaining one-half has moved onto the surface S of MOD 22. At this point, the magnetic drive system 70 of MOD24 moves in the Y direction, towards and beyond guide member G4, whereby contact between the side of rack R' and guide member G4 acts to strip the drive mechanism from magnetic engagement with the rack. The magnetic drive system of MOD 22 is then moved to a position in which it magnetically engages the rack at rack-transfer station 52 and transports it over the surface S of MOD 22 as required. It will be appreciated that rack-transfer between the specimen-transport modules can be effected on either of paths E or F, as determined by the system controller 20, which controls the traffic pattern of the racks throughout the module (and workcell). Preferably, however, one path is used to transfer racks in one direction, and the other path is used to transfer racks in the opposite direction. Not shown in the drawings is a pair of photoelectric sensors that detect the presence of a rack at each of the rack-transfer stations. When a rack that is to be transferred to another specimen-transport module is transported to either of the opposite end of paths E or F of a rack-transferring module, its presence is sensed by a sensor at the rack-transfer station of the transferring module. When a rack is also detected at the rack-transfer station by the sensor of the rack-receiving module, the rack is now in a position to be acted upon by the X/Y transport system of the receiving module. The system controller acts on the output of these sensors to send the XY drive mechanism of the receiving module to further transport the rack therein.

Figure 7:
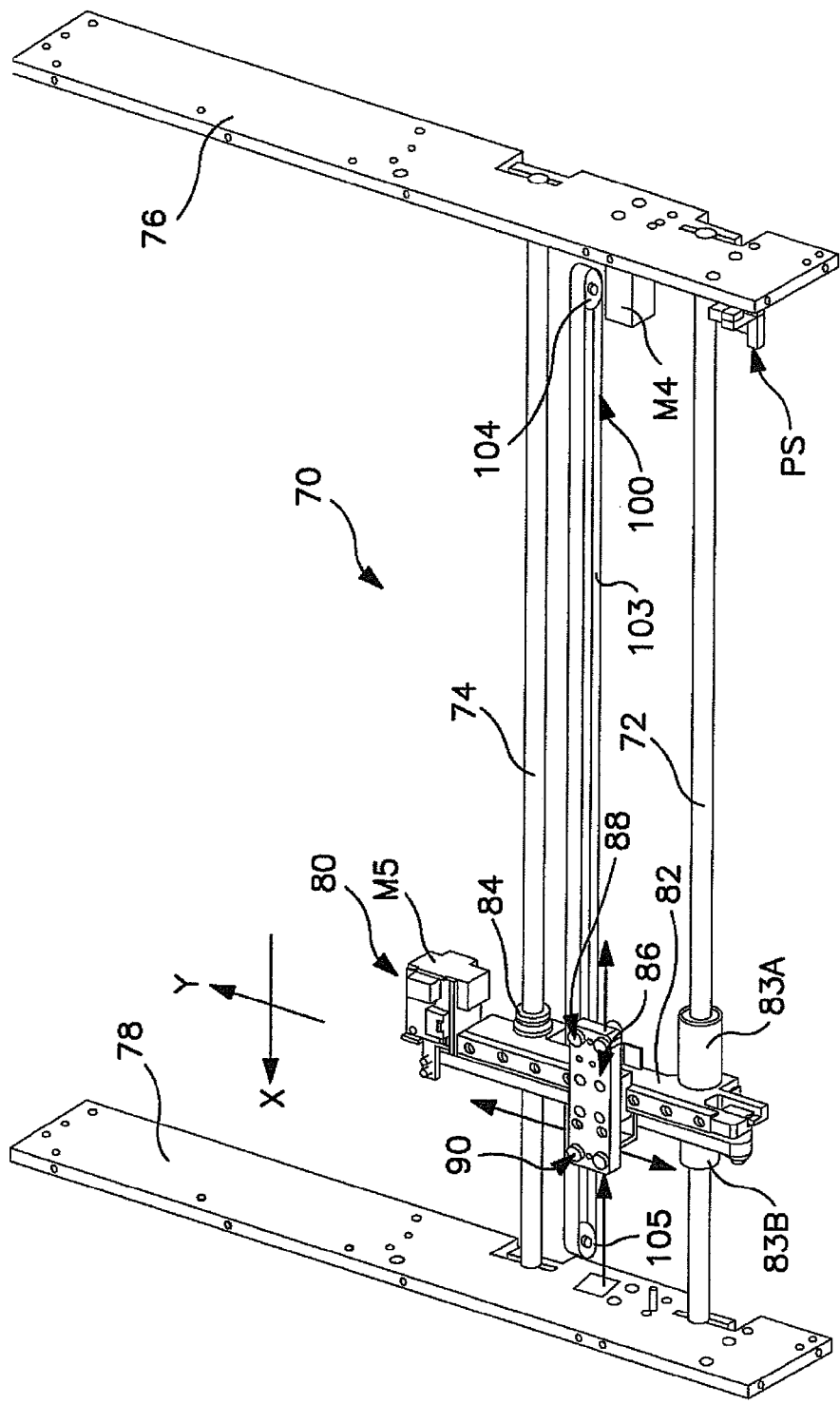
FIG. 7 is a perspective illustration of an X/Y drive mechanism for controlling the X/Y position of an individual specimen-container rack in the specimen-processing portion of the specimen-transport module of the invention.

FIG. 7 illustrates a preferred X/Y drive mechanism 70 for moving specimen-container racks in mutually perpendicular directions across surface S of the specimen-transport module described above so as to position a rack at any desired location along the transport paths D, E and F shown in FIGS. 3 and 4. This X/Y drive mechanism is the subject matter of the above-referenced U.S. Pat. No. 7,028,831, entitled "Magnetic Specimen-Transport System for Automated Clinical Instrument." Drive mechanism 70 is adapted to be mounted within the module housing H directly beneath and in close proximity to the underside of the non-magnetic plate P on which the specimen-container racks are supported for movement. Generally, the drive mechanism operates to advance specimen-container racks on surface S by producing an X/Y movable magnetic field below surface S (i.e., below plate 60). As explained below, the magnetic field is produced by one or more permanent magnets carried by an X/Y movable magnetic truck assembly 80. The magnetic field produced by each magnet passes through the non-magnetic support plate P of the transport module and magnetically couples with one or more (preferably two) magnetically-attractive members carried in the base portion of each specimen-transport rack. The magnetic bond between the magnets and magnetically-attractive members is sufficiently strong that, as the magnetic truck assembly moves in the X/Y plane, a magnetically-coupled rack follows.

Figure 8A:
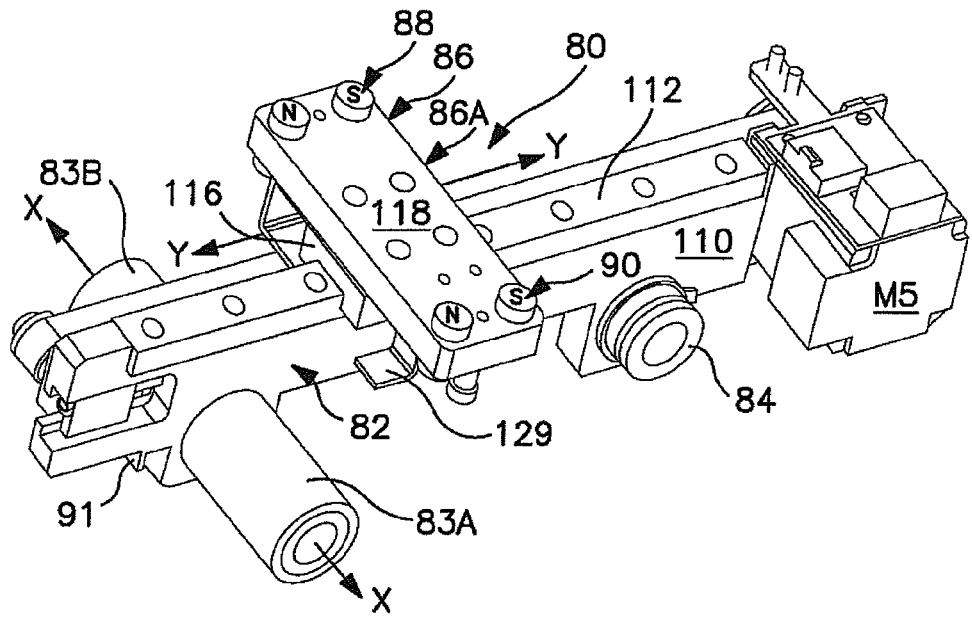
FIGS. 8A and 8B are enlarged perspective views of the Y-drive portion of the FIG. 7 apparatus.
Figure 8B:
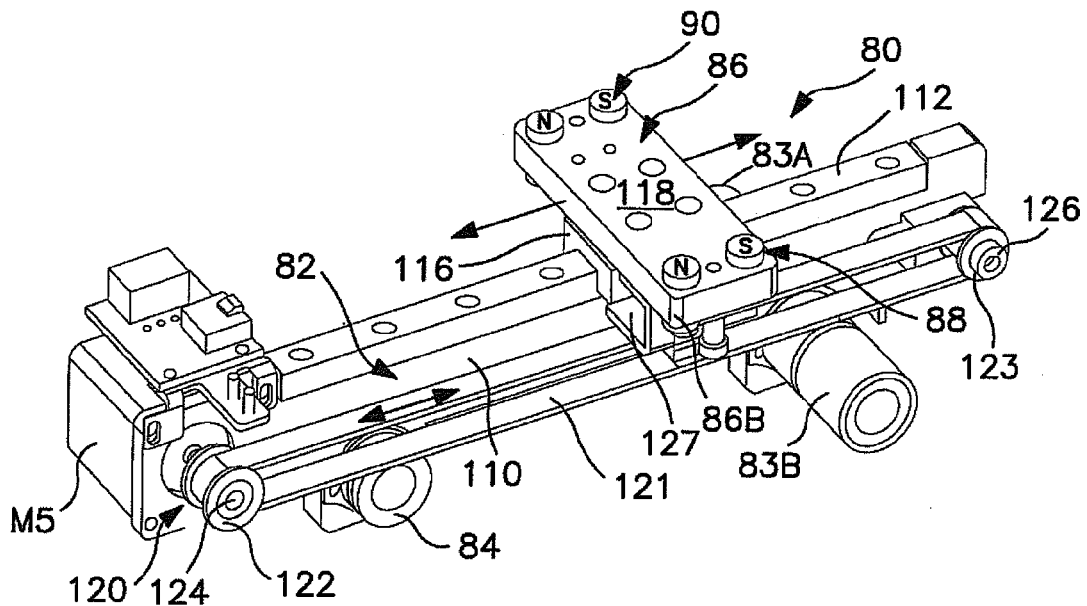

In FIG. 7, the preferred X/Y drive mechanism 70 is shown to comprise a pair of spaced and substantially parallel support shafts 72, 74 that are supported at their respective ends by the opposing side walls 76, 78 of the module housing H. A preferred spacing between shafts 72 and 74 is about 16 cm. As shown, shafts 72 and 74 extend parallel to the X coordinate and, together, they support the above-noted magnetic truck assembly 80 for sliding movement parallel to the X coordinate. As best shown in FIGS. 8A and 8B, truck assembly 80 comprises a truck-support housing 82 in which three sleeve bearings 83A, 83B and 84 are mounted. Bearings 83A and 83B are positioned on opposite sides of the truck-support housing, and they are aligned to slide on shaft 72, the so-called "datum" shaft. The respective outboard edges of bearings 83A and 83B are relatively far apart, e.g., about 10 cm., to assure that the truck-support housing 82 remains perpendicular to the datum shaft at all times during its travel therealong. Bearing 84 is supported in a horizontal slot formed in the truck-support housing, and this bearing rides along shaft 74 (the "anti-rotation" shaft) during movement of the truck assembly in the X direction. The slot mounting enables bearing 84 to slide smoothly along the anti-rotation shaft even though the latter may not be perfectly parallel to the datum shaft; at the same time, however, the slot mounting prevents the truck-support housing from pivoting (about the datum shaft), thereby assuring that this housing remains in a horizontal (X/Y) plane at all times during movement of the truck assembly along the datum shaft. As explained below, the truck-support housing itself supports a permanent magnet-bearing truck 86 for sliding movement parallel to the Y coordinate. Preferably, truck 86 carries a pair of U-shaped magnets 88, 90 that magnetically interact and couple with a pair of magnetically-attractive members 170 (shown in FIG. 12) carried in the base portion of each specimen-container rack. Such magnetic interaction between the magnets and the magnetically-attractive members 170 is sufficiently strong to cause the specimen-container racks to slide across surface S and to follow the movement of the magnetic truck 86 beneath surface S. Thus, by the arrangement described, the X/Y position of a specimen-container rack atop surface S is determined by the X/Y position of the magnetic truck 86 beneath surface S.

As shown in FIG. 7, movement of the magnetic truck assembly in the X direction (i.e., along shafts 72 and 74) is effected by a belt drive mechanism 100 mounted between the module housing walls 76 and 78. Drive mechanism 100 comprises an endless belt 103 that spans between a drive pulley 104 and idler pulley 105. Drive pulley 104 is rotatably driven by the drive shaft of an X-drive motor M4 mounted on housing wall 76. Motor M4 is a bi-directional stepper motor that operates under the control of the system controller 20. A tab 91 located at one end of the truck-support housing 82 is sensed by a photoelectric sensor (not shown) mounted on housing side wall 76 to provide a "home" position for the X-drive mechanism and a point of reference for the X-position of the magnetic truck 86.

Referring to FIGS. 8A and 8B, the truck-support housing 82 of the magnetic truck assembly 80 comprises an elongated bar 110 in which the above-noted sleeve bearings 83A, 83B and 84 are mounted. Bar 110 supports a linear rail 112 along its uppermost surface. Rail 112 extends in a direction perpendicular to the respective longitudinal axes of the sleeve bearings; thus, when the sleeve bearings are mounted on their respective shafts, rail 112 extends parallel to the Y coordinate. Rail 112, in turn, slidably supports the above-noted permanent magnet-bearing truck 86. The latter comprises a channel-shaped member 116 which is adapted to slide along rail 112. Member 116 is rigidly connected to a non-magnetic plate 118 on which the permanent magnets 88 and 90 are mounted, as described below. As best shown in FIG. 8B, plate 118 is selectively driven along rail 112 by a belt drive mechanism 120. The latter comprises an endless belt 121, a pair of pulleys 122, 123, and a bi-directional stepper motor M5 which communicates with and is controlled by the system controller 20 via a flex cable, not shown. Pulley 122 is rotatably driven by the drive shaft 124 of motor M5, and idler pulley 123 is mounted for rotation on a fixed shaft 126 extending from bar member 110. The respective axes of shafts 124 and 126 extend parallel to the X coordinate. Belt 121 is trained about the drive and idler pulleys as shown, and it is operatively connected to the magnetic truck assembly 94 by a bracket 127, best shown in FIG. 9. Thus, it will be appreciated that as the drive shaft of stepper motor M5 rotates, belt 121 advances over pulleys 123 and 123 and, owing to the connection of the belt and the magnetic truck assembly 94, the position of the permanent magnets carried by plate 118 in the Y direction is determined by the axial position of the stepper motor drive shaft. A flag member 129 depending from the bottom surface of plate 118 is sensed by a photoelectric sensor PS (shown in FIG. 7) mounted on side wall 76 of housing H to determine the "home" position of the Y-drive mechanism, and thus provides a point of reference for the Y position of the magnetic truck. The X and Y sensors on the housing frame are positioned such that X home position of the truck is sensed first, and then its Y home position is sensed.

Figure 9:
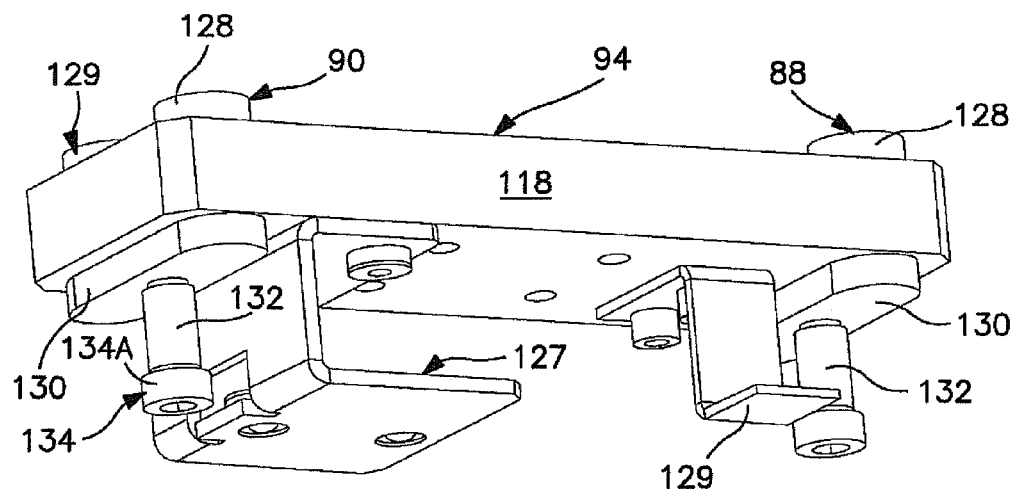
FIG. 9 is an enlarged bottom perspective view of the magnetic X/Y truck used in the FIG. 7 apparatus to magnetically engage a specimen-container rack.

Still referring to FIG. 9, each of the permanent magnets 88 and 90 comprises a pair of cylindrical bar magnets 128, 129, that are connected by a flux bridge 130. The bar magnets are received by cylindrical bore holes formed in plate 118, and they are positioned such that opposite magnetic poles (north/south) extend above the plate surface. The permanent magnets are biased upwardly by a spring 132 that surrounds a shoulder bolt 134, threaded into the base of plate 118 and extending downwardly, through a clearance hole formed in the flux bridge. One end of the coil springs is supported by the bolt head 134A, and the opposite end of the spring engages the flux bridge and thereby urges the flux bridge into contact with the underside of plate 118. Preferably, each of the bar magnets has a diameter of about 8 mm., and magnets are spaced apart by about 8.8 mm., center-to-center. The length of each magnet is such as to protrude about 3 mm above the plate 118 when the flux bridge contacts the underside of the plate. Preferably, each of the magnets comprises neodymium-doped iron. The flux bridge is made of iron and is about 9.5 mm. in thickness. Preferably, the XY drive system 70 is positioned so that a spacing of about 1 mm. is provided between the top of the bar magnets and the bottom of the rack-support plate P.

Figure 10:
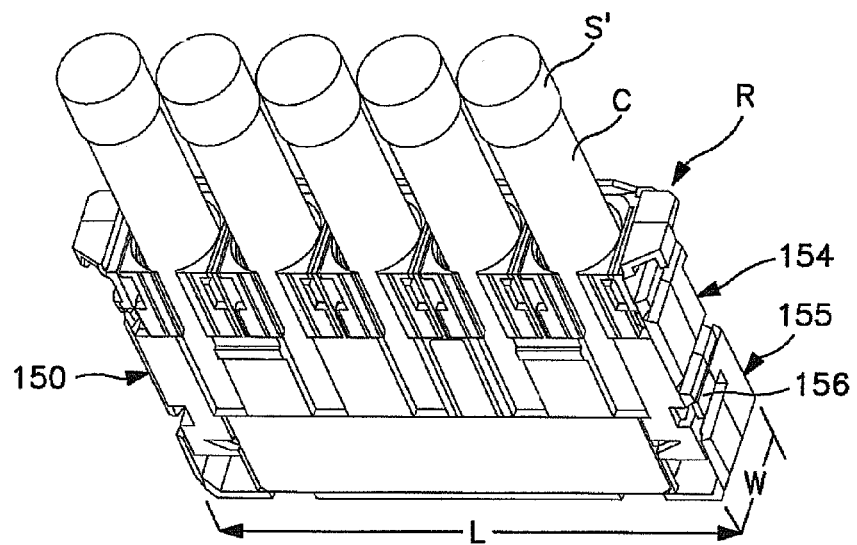
FIG. 10 is a perspective view of a preferred specimen-container rack containing a plurality of specimen containers.

Referring now to FIG. 10, a preferred specimen-container rack R adapted for use in the specimen-transport apparatus described above is shown as comprising a housing 150 that defines plural (in this case five) compartments 152 for receiving a like plurality of specimen containers C. The particular rack shown is the subject matter of the above-referenced U.S. application Ser. No. 10/794,685 entitled "Specimen-Container Rack for Automated Clinical Instrument."

In the embodiment shown, housing 150 is made of plastic and comprises two interlocking sections, an upper section 154 that defines the container compartments 152, and a base section 155 that provides support for the specimen containers received by the rack, and further serves to house the above-noted magnetically-attractive members 170. The two sections are snapped together and held in place by a pair of flexible arms 156 provided at opposite ends of the base section. In FIGS. 11A and 11B, the upper section of the rack is shown as comprising a pair of parallel end walls 157 disposed at opposite ends of a forward wall 158 and a rear wall 159. A plurality of equally-spaced transverse walls 160 extend between the front and rear walls. The transverse walls operate to separate each the container compartments 152. At the top of each compartment, a container-centering assembly 162 is provided. The latter serves to releasably engage and to center specimen containers of different diameters within the compartments, whereby the central longitudinal axes of the received containers are equally spaced and arranged in parallel in a common plane. Thus, when such a specimen-container rack is registered in its specimen-aspiration position within a specimen-transport module, the aspiration probe assembly can repeatedly and reliably access the center of each of the specimen containers by moving sideways (along the X coordinate) in a vertical plane. Details of the centering assemblies 162 are described in the commonly assigned U.S. Pat. No. 5,687,849, incorporated herein by reference. The engaging force between the container centering assembly and the container is sufficient to prevent the container from rotating or moving axially during the specimen-mixing operation when the containers are repeatedly inverted.

As shown in FIG. 11B, the rear, vertical edge of walls 157 and 160 are provided with structure that accommodates the afore-mentioned, horizontally-extending tongue member 47A that protrudes from the wall 47 of the mixing device 46. Such structure takes the form of series of spaced notches 157A, 160A and 160B. Whereas notches 157A and 160A are rectangular in shape and provide clearance for the tongue member 47A, notches 160B have a trapezoidal shape that is adapted to engagingly receive the opposing edges of the tongue member 47A (which has a trapezoidal transverse cross-section), as the rack is caused to slide horizontally along the surface of mixing plate 47 by the magnetic transport system described above. Preferably, the trapezoidal notches are formed in the edges of walls 160 that separate the first and second compartments 152, and the forth and fifth compartments 152. The dimensions of the rectangular notches 157A and 160A are such as to enable the tongue member 47A to slide unimpededly along wall 47 to engage the notches 160B. Upon completing engagement between the two notches 160B and tongue 47A, the specimen-container rack is in a position to be inverted by the mixing device 46, causing the contained specimens in the rack to be mixed, and to have the aspiration probe assembly PA of an associated clinical instrument access any one of the specimen containers supported by the rack. The details of the specimen mixer are discussed further below.

Figure 12:
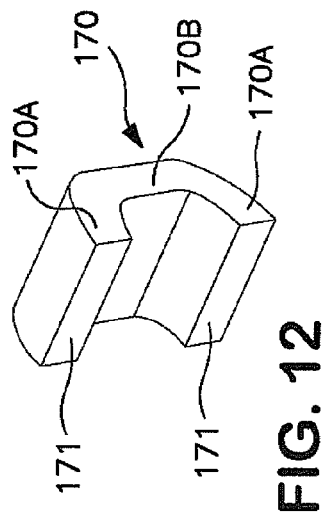
FIG. 12 is a perspective illustration of a magnetically-attractive member that is adapted to be mounted within the bottom portion of the rack shown in FIGS. 11A and 11B.

According to another aspect of the above-referenced application, the base section 155 of rack housing 150 is structured to receive and support a pair of U-shaped, magnetically-attractive members 170 (best shown in FIG. 12). Preferably, each member 170 comprises magnetically-attractive stainless steel 440C. Each member 170 comprises a pair of spaced leg portions 170A that are connected together at one end by a bridge portion 170B. Members 170 are supported in the rack's base portion so that the distal ends 171 of their respective leg portions 170A extend downwardly, toward the bottom surface 155A of the rack. As shown in FIG. 11B, the bottom surface of the rack defines four rectangular pads 172 which protrude downwardly, by about 0.5 mm., at the four corners of the rack. These pads provide the only physical contact between the rack and the transport surface S. Preferably, the distal ends 171 of members 170 terminate at the bottom surface of the rack, i.e., about 0.5 mm short of the plane defined by the distal ends of pads 172. The spacing between the distal ends 171 corresponds to the spacing between the pole tips of the permanent magnets 96 and 98 carried by the magnetic truck 80. Preferably, this spacing is about 9.5 mm. Thus, when a specimen-container rack is resting on its pads 172 atop surface S with the distal ends of members 170 being juxtaposed to the pole tips of magnets 96 and 98, a magnetic circuit will be completed, with the flux emanating from one magnetic pole tip passing through member 170 and entering the opposite pole tip. The strength of the magnetic pole pieces is selected to provide a sufficient magnetic coupling between the rack and the drive mechanism to impart motion to the rack as the magnetic drive moves below surface S. The provision of opposing U-shape structures, one for the permanent magnets 96 and 98 and the other for the magnetically-attractive members 170, gives rise to a magnetic coupling that strongly resists lateral decoupling forces by maximizing the ratio of the lateral forces to the vertical forces.

A further feature of the base section 155 of rack R is shown in FIGS. 11A and 11B. Base section 155 further defines a pair of cup-shaped pockets 165A and 165b that are located at opposite ends of the rack. Each of the pockets is adapted to receive a movable "foot" member comprising a redundant rack-drive mechanism (described below with reference to FIG. 22). As noted above, such a drive mechanism is contained within housing 60 of the specimen-transport module; it is used to advance racks along path F (in FIG. 4) in the event the magnetic drive mechanism underlying surface S is either not being used, or it is otherwise occupied when it is desired to bypass a particular specimen-transport module by advancing racks along path F. The foot member of the redundant drive mechanism, upon entering either pocket 165A or 165B of a rack positioned at either one of the rack-transfer stations 52 or 54, exerts a lateral force on the end wall 155A of the base portion 155 and thereby advances a rack by pulling it edgewise along path F.

Figure 13:
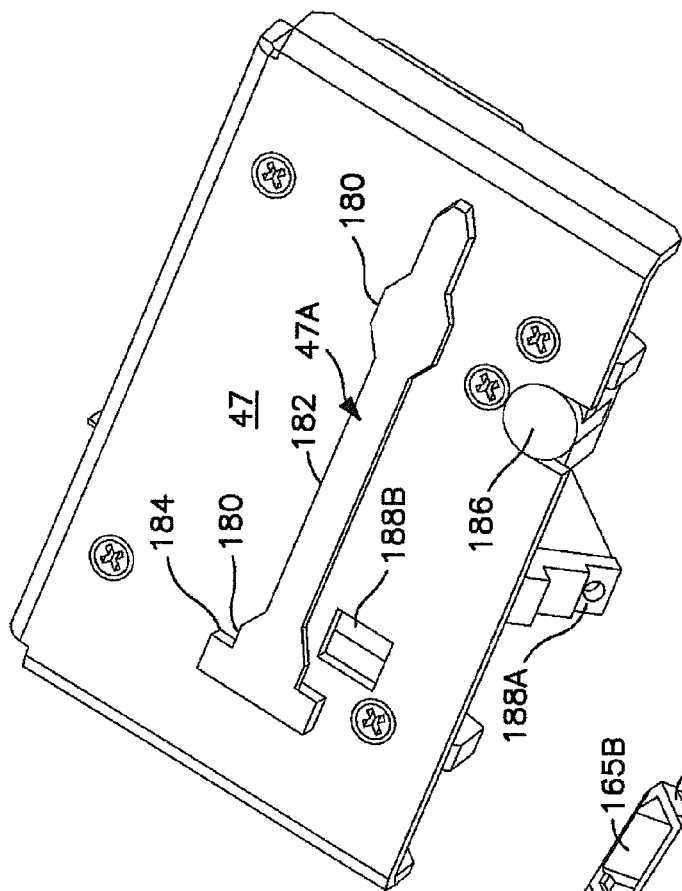
FIGS. 13 and 14 illustrate a preferred mating structure by which a specimen-container rack is operatively coupled to a mixing device of the specimen-transport module of the invention.
Figure 14:
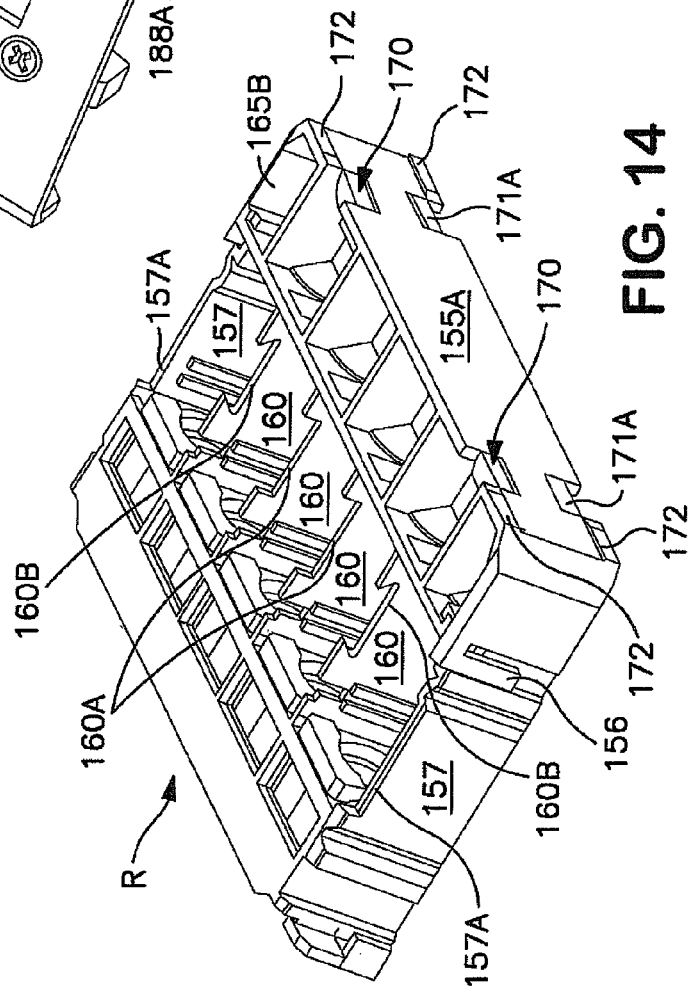

In FIGS. 13 and 14, the preferred tongue-and-groove mechanism by which the mixing device 46 firmly engages each rack for specimen-mixing purposes is more clearly illustrated. As mentioned above, the mixing device 46 comprises a movably-mounted plate 47 against which the individual racks are positioned by the X/Y drive mechanism prior to mixing. Prior to mixing, plate 47 is in a vertical plane and thus positioned to receive and be coupled to a rack. As shown in FIG. 13, plate 47 supports a horizontally-extending tongue member 47A having a pair of rack-engaging regions 180 that are separated by a somewhat narrower central region 182. The transverse cross-section of regions 180 is trapezoidal in shape and is of a size adapted to mate with the two notches 160B formed in the rack walls 160 during relative sliding movement between the rack and the surface of plate 47. Such movement, of course, is provided by afore-described drive mechanism 70. A stop surface 184 formed at one of the distal ends of member 47A operates to arrest sliding of a rack along wall 47 by engaging the transverse wall 160 separating the first and second container compartments. At this point, regions 180 are engaged with notches 160B and a permanent magnet 186 mounted on plate 47 magnetically attracts one of the magnetically-attractive members 170 carried by the rack base 155. The position of such magnet is slightly offset (not directly opposite) member 170 so that the magnet exerts a lateral force component acting to urge the stop surface 184 into engagement with the transverse wall that operates to resist further movement of the tongue into the notches 160B. The magnetic attraction between magnet 186 and the magnetically-attractive member 170 is sufficiently strong to prevent the rack from moving laterally on the tongue regions 180 during the mixing operation to follow. Yet, the magnetic interaction between magnet 186 and member 170 is sufficiently weak so as to be readily overcome by the magnetic force exerted on the rack by the X/Y movable magnetic truck when the time comes to disengage the rack from the mixing mechanism. A photoelectric sensor 188A supported by surface S detects racks through a window 188B formed in plate 47 and transmits a signal to the system controller indicating that a rack is positioned on the plate for mixing and that the plate 47 is vertically oriented.

Figure 15A:
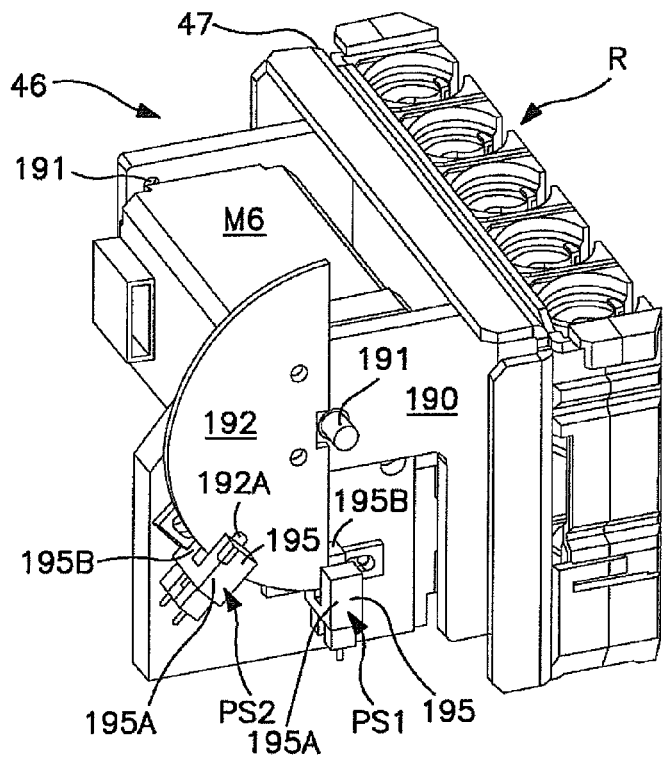
FIGS. 15A and 15B are perspective illustrations of a specimen-mixing device illustrating the position of the specimen-container rack in generally upright and partially inverted positions.
Figure 15B:
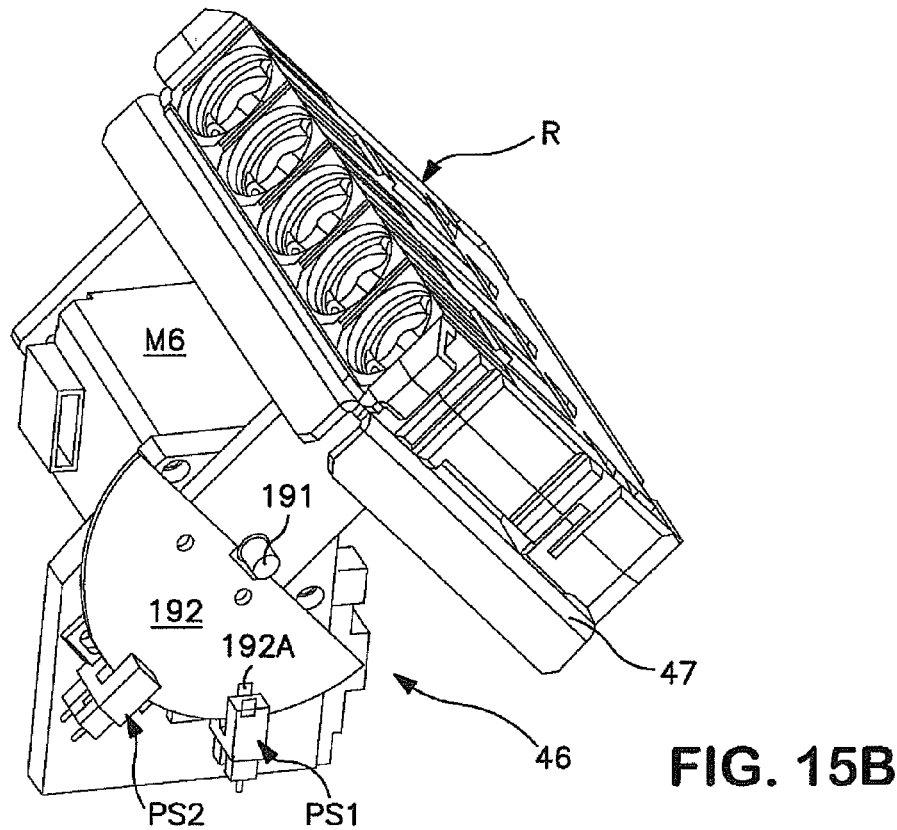

In FIG. 15A, a rack is shown as operatively coupled to the mixing plate 47 prior to mixing. Plate 47 is supported by a yoke assembly 190 that is supported for rotation on the drive shaft 191 of a bi-directional stepper motor M6 that operates under the control of the system controller 20. The angular position of plate 47 as it moves about the drive shaft axis is sensed by a pair of photoelectric sensors PS1 and PS2 The latter are positioned at selected positions about the periphery of a semi-circular disk 192 that is rigidly attached to yoke 190 as the yoke rotates with drive shaft 191. Each photoelectric sensor comprises a yoke-shaped housing 195 that supports a light-emitter and a light-sensor between opposing and spaced arms 195A and 195B. The respective yoke arms of the photoelectric sensors are positioned on opposite sides of the disk 192 in a position to sense the passage of a notch 192A formed in the disk periphery. The photoelectric sensors are angularly spaced by 45 degrees about the disk periphery and located so that, when the rack is in a vertical position, as shown in FIGS. 15A and 16A, both sensor detect light from their respective light emitters, a condition in which both sensors are "ON". PS1 senses the emitted light unobstructed by the disk, and PS2 senses the emitted light as it passes through the notch 192A. When the motor shaft 191 has rotated to a 45 degree "cap-up" position, as shown in FIGS. 15B and 16B, PS1 senses light passing through the notch 192A, and PS2 senses no light since it is blocked by the disk; thus, PS1 is ON, while PS2 is OFF. As the drive shaft continues to rotate counter-clockwise, as viewed in FIGS. 16A and 16B, both photoelectric sensors are in an OFF state until the trailing edge of disk 192 passes sensor PS2, at which time PS1 is OFF while PS2 is ON. At this time the container C has been inverted to a 45 degree "cap-down" position. In the cap-down position, the air bubble in the container will have shifted to the bottom of the container, thereby substantially mixing the liquid specimen in the container. Having reached the cap-down position, the stepper motor reverses, and the container is returned to its 45 degree cap-up position, thereby re-inverting the container and its contents. This cycle is repeated several times. Preferably, a specimen rack is rotated between its cap-up and cap-down positions eight times before a specimen is aspirated from the first container in the rack. While this specimen is being processed, the rack is inverted two more times, and this process is continued until the last specimen in the rack has been aspirated. Thus, the last specimen to be aspirated in a rack having five containers will be inverted sixteen times prior to aspiration.

The above description completes the discussion regarding the manner in which specimen container racks are normally transported through and processed by the processing section 44 of the specimen transport module of the invention. The description below relates to preferred mechanisms for advancing unprocessed specimen-container racks within the input buffer 40 to a position in which a rack can acted upon by the transport mechanism of the processing section, and for transporting processed specimen-container racks within the output buffer 42 to an off-loading position. Further discussed below is a redundant drive mechanism, contained by housing 60 for advancing racks along path F so as to by-pass a particular specimen-transport module.

Figure 17A:
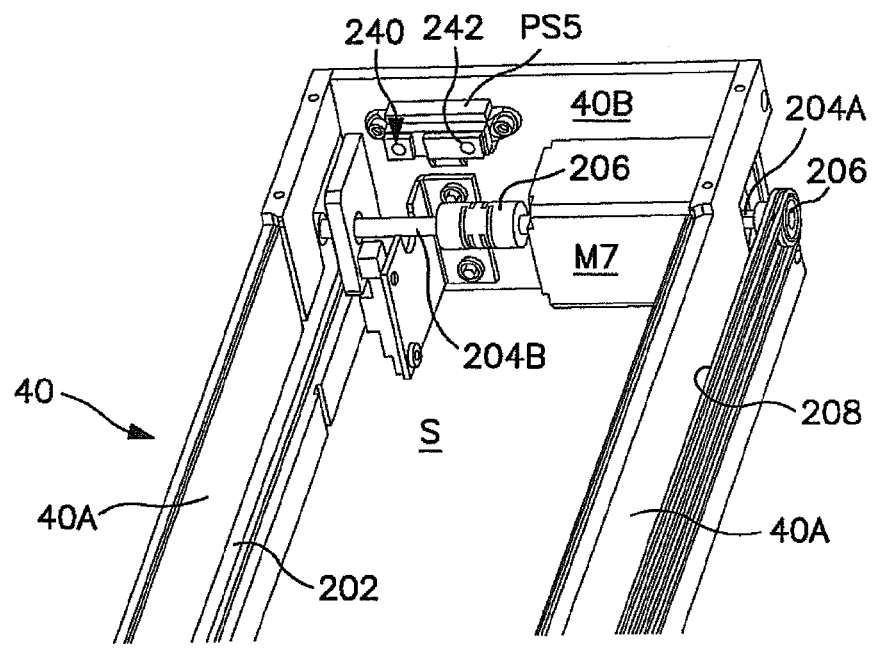
FIGS. 17A and 17B are perspective views of the rear and front portions, respectively, of the input buffer portion of the specimen-transport module of the invention.
Figure 17B:
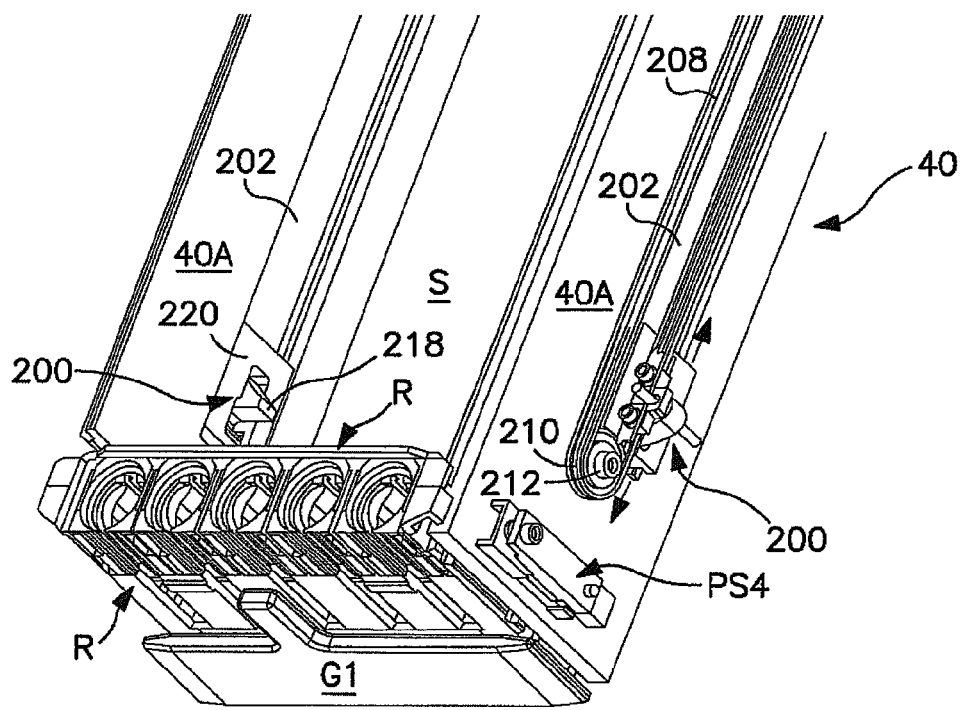

Referring now to FIGS. 17A and 17B, these drawings respectively illustrate certain preferred details of the rear and front portions of input buffer 40 of the FIG. 3 apparatus. Preferably, the racks are supported in the buffer on the same surface S on which they are transported through the processing section 44 of the specimen transport module. The buffer side walls 40A are spaced apart slightly greater that the length L of the specimen-container rack, and the racks are urged towards the front of the buffer and into contact with guide member G1 by a pair of cam-actuated pushers 200 that are movably mounted on the buffer side walls. The pushers are selectively moved in synchronism forward and backwards in a track 202 formed in each of the buffer side walls by a bidirectional stepper motor M7 that operates to rotate a pair of opposing drive shafts 204A and 204B. Drive shaft 204B is extended by a coupling 206 which further serves as a means for adjusting the synchronized movement of the two pushers. Each of the respective free ends of the drive shafts supports a drive sprocket 206. The latter is located outside the buffer side walls and functions to advance a cable 208 (actually a so-called "cable chain") which is supported between the drive sprocket and an idler sprocket 210. The idler sprocket is mounted for rotation on a shaft 212 located on the outside of the buffer side wall towards the front of the buffer. Opposite ends of each cable are connected to the cam-actuated pusher 200 by a pair of clamps 214, best shown in FIGS. 18A and 18B. When the drive motor operates to advance the cables in a direction acting to pull the pushers 200 towards the front of the buffer, a rack-pushing finger 218 protrudes outwardly from a pusher housing 220 and extends inwardly from the buffer side wall to a location in which its surface 218A will contact the rear side of a rack located within the buffer. Continued movement of the pushers with the fingers 218 extended as shown in FIG. 18A will serve to move a rack, and any racks in front of it in the input queue, towards guide member G1. When a rack reaches the position shown in FIG. 17B, a photoelectric sensor PS4 mounted on the buffer side wall will sense the presence of a rack at such location and transmit a signal to the system controller 20 to stop further movement of the pusher. When additional racks are received by the input buffer, motor M7 operates in the reverse direction, thereby pulling the pushers towards the rear of the buffer. When the cable 208 pulls on the pusher mechanism in the reverse direction, the fingers 218 retract into the pusher housing 200, to the position shown in FIG. 18B.

Referring to FIGS. 18A and 18B, it will be appreciated that the pusher finger 218 are an integral part of a cam member 222 (shown in FIGS. 19A and 19B) that is adapted to rotate about an axis A'. The cable clamps 214 are rigidly connected to a housing 224 having a slot 224A that receives an actuating pin 226 by which the cam member can be rotated. As the cable 208 pulls the pusher in a forward direction, housing 224 exerts a force on the actuating pin causing the cam member to rotate clockwise, as viewed in FIG. 19A, about axis A'. As the cam rotates to the position shown in FIG. 19A, in which position the pusher finger 218 is fully extended, the cam surface 222A engages a positive stop 228 within housing 200. Continued force applied by the cable then results in movement of the entire pusher mechanism along the linear track 202. The slot 224A in housing 224 enables the actuating pin to move sideways, as it must during the rotation of the cam member. When the drive motor reverses, thereby causing the opposite cable end to produce a counter-clockwise rotation (as viewed in FIG. 19B) of the cam member, the cam rotates to the finger-retracted position shown in FIG. 19B. When the cam rotates to this position, the pusher finger surface encounters a second positive stop 230 within housing 200. Continuing the force applied by the cable on the actuating arm 226 results in movement of the entire pusher mechanism in the opposite direction along track 202, i.e., towards the rear of the input buffer. The system controller keeps track of the number of cassettes in the input buffer by means of a photoelectric sensor PS5 mounted on the rear wall 40B of the input buffer. (See, FIG. 17A). Such sensor comprises a light transmitter 240 and a light detector 242, the latter serving to detect the transmitted light upon reflection by the rear surface of the last rack in the input queue. A standard triangulation method is used to compute the distance of the last rack from the photoelectric sensor and, hence, the number of racks in the buffer. In operation, whenever a rack is placed anywhere in the input buffer, sensor PS5 will sense that the distance between it and the preceding distance measured has changed. Motor M7 will then operate to retract the pusher finger and move the pusher to a location behind the last rack received. The motor will then rotate in the opposite direction, causing the pusher finger to be extended and to drive the pusher finger into engagement with the back of the last rack. The pusher will then move forward until either the first rack in the input queue has reached the photoelectric sensor PS4, or until the pusher reaches the end of the track 202. Note, the forward movement of the pusher is limited to a position in which it will push a stack of three racks to a position in which the first rack will be sensed by sensor PS4. The X/Y truck is capable of moving (in the Y direction) into the input buffer by a distance of three rack widths W, e.g., to extract the last three racks of a test run.

Referring now to FIGS. 20A and 20B, a preferred output buffer 42 is illustrated as comprising another type of rack-pushing mechanism 250 for discharging processed specimen-container racks into the output buffer. Upon aspirating and processing the specimens of a given rack, the afore-described X/Y magnetic drive mechanism operates to advance the rack edgewise, in the X-direction, along path D, to a position directly opposite the output buffer. The X/Y drive then operates to move the magnetic truck 86 rearwardly, in the Y-direction, by a distance W' (about 30 mm.) that is slightly greater than the width W of a rack. In doing so, the rear-most edge 86A (shown in FIG. 8A) of the truck physically engages a strike plate 255, best shown in FIG. 21. (Note, in FIGS. 20A and 20B, the support plate P is not shown, and only those features of the output buffer above and below the plate are shown.) The strike plate 255 is located below the rack-support plate P and in the path of travel of the magnetic truck. Strike plate 255 is rigidly connected, by an upwardly-extending tab 255C, to one leg 257A of an L-shaped pusher member 257 which is located atop surface S. Leg 257A is mounted for sliding movement along the bottom edge of buffer wall 42A; hence, leg 257A extends in the Y-direction. The other leg 257B of the pusher member extends perpendicular leg 257A, i.e., in the X-direction. The strike plate is spring biased by a coil spring 259 towards a home position shown in FIG. 20A. In this position, the leg member 257B directly underlies the guide member G3 shown in FIG. 3.

Assuming no racks are present in the output buffer, the magnetic truck will operate to advance a rack into the buffer by only the magnetic attraction between the truck 86 and the rack. As truck 86 moves rearward in the Y-direction, however, its rear-most edge physically engages the straight edge portion 255A of the strike plate and thereby moves the strike plate rearwardly, against the spring force provided by spring 259. After the strike plate moves rearwardly by a distance W', the free end of leg 257A nearly reaches the edge 260A of a notch 260 formed in the lower portion of wall 42A. Having reached this point, the system controller directs the truck to move in the X-direction, away from the output buffer and towards the input buffer. In doing so, the magnetic attraction between the truck and rack is overcome, since the rack will be prevented from following the truck due to its contact with buffer side wall 42B. As the truck continues to move in the X-direction away from the output buffer, the rear corner 86B of the magnetic truck, shown in FIG. 8B, will begin to engage the diagonal edge 255B of the strike plate. As the truck further continues its movement in the X-direction, the strike plate gradually returns to its home position as the truck corner 86B rides along the diagonal surface of the strike plate.

Now, assuming that one or more processed racks are already present in the output buffer when a newly processed rack is ready for discharge, the same process as described above is repeated. However, the driving force for moving a stack of racks rearward into the output buffer is the force applied by leg 257B of the pusher member 257. Note, the magnetic attraction between the truck 86 and a single rack is not sufficiently strong to push a stack of racks on surface S. Thus, by the arrangement described, multiple racks in an output queue are indexed rearwardly by the approximate width of one rack as the magnetic truck 86 physically engages the strike plate and its associated pusher member and moves rearward by a distance W'. A pair of photoelectric sensors PS6 and PS 7 mounted on the buffer wall 42A sense when the output buffer has received a rack, and when the output buffer is full, respectively.

Figure 23:
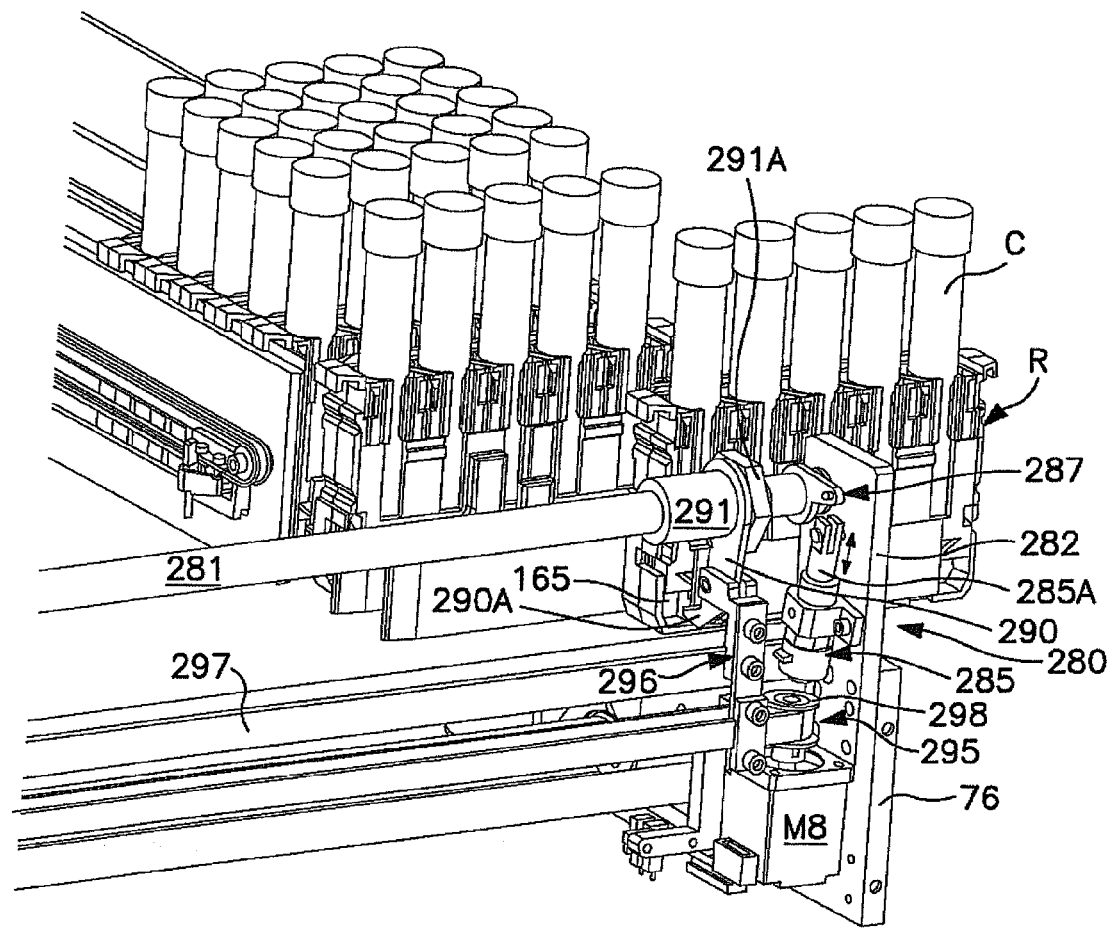

In a workcell environment where several different clinical instruments are transferring specimen-container racks between their respective specimen-transport modules in the manner described above with reference to FIG. 6, circumstances may arise that make it either desirable or mandatory to bypass the X/Y drive mechanism 70 of a particular instrument in order to transport a specimen-container rack from one instrument to another. For example, in a three instrument workcell where the X/Y drive mechanism of the middle instrument is not functioning, it is desirable to provide the workcell with the capability of continued operation if the processing needs of a given sample. Thus, in accordance with another aspect of this invention, a redundant drive mechanism 280, illustrated in FIGS. 22 and 23, is provided in each specimen-transport module for advancing a specimen-container rack through the module, from one of its rack-transfer stations to another, independently of the X/Y transport mechanism of the module. Such redundant drive mechanism is housed within the forward housing 60 of each module, and it extends between the rack-transfer stations 52 and 54.

Referring to FIG. 22, drive mechanism 280 comprises a spline shaft 281 of non-circular (e.g., star-shaped) transverse cross-section. The spline shaft extends between a pair of parallel support plates 282 and 283 which are rigidly connected to the module side walls 76 and 78. Plates 282 and 283 contain bearings that serve to rotatably support the spline shaft for rotation about its longitudinal axis. The rotational position of shaft 281 is controlled by a linear actuator 285 mounted on wall 282. Actuator 285 comprises a linear actuator member 285A which moves axially between an extended position, shown in FIG. 23, to an unextended position closer to the linear actuator housing. A mechanical linkage 287 connects the actuator with the spline shaft 281. Thus, as the linear actuator moves about 12 mm. between its extended and non-extended positions, the spline shaft rotates through an angular range of about 30 degrees. The spline shaft slidably supports a plate 290 having a rack-engaging foot member 290A. Plate 290 is provided with a central opening (not shown) that is shaped to receive and slidingly engage the spline shaft. Plate 290 is clamped between the spline shaft truck 291 and a nut 291A, both of which are slidably supported by the spline shaft and adapted to rotate therewith. Thus, when the spline shaft is caused to rotate by the retracting movement of the linear actuator, plate 290 will rotate with the shaft and, in doing so, foot portion 290A will move in the Y direction, towards the rear of the module. If a specimen container rack R is positioned as shown in FIG. 23, the foot. Member 290A of plate 290 will enter one of the rack-pockets 165A or 165B. Since the width of the foot 290A is considerably less than the width of the rack-pocket, it is a relatively easy task in practice for the foot to enter the pocket. Upon entering the rack-pocket, the foot portion is now ready to drivingly engage the side wall of the pocket and thereby advance the rack along path F of the specimen-transport module. When the linear actuator member moves to its extended position, the spline shaft will rotate in the opposite (counter-clockwise) direction causing foot member 290A to move out of the rack-pocket, to a position that enables the spline shaft truck to move unimpededly along the spline shaft.

To advance a rack along path F, plate 290 is slidably driven along the spline shaft by a belt-drive system 295. The belt drive system comprises a bi-directional stepper motor M8 that is mounted on the module side wall 76. Motor M8 is controlled by the system controller 20 and operates to selectively advance an endless belt 297 that is trained about a drive pulley 298 and an idler pulley 299. The drive pulley is mounted on the drive shaft of the stepper motor, and the idler pulley 299 is mounted for rotation on a fixed shaft supported by the base of a belt-tensioner housing 300 mounted on the shaft-support plate 283. As shown, belt 297 extends in the X-direction, parallel to path F of the module. Plate 290 is mechanically connected to the drive belt via a linkage 296.

In operation, the redundant drive mechanism 280 can be used to bypass a module by mechanically advancing a rack from the position shown in FIG. 23, i.e., in a position in which the rack R spans the opposing transfer stations of adjacent specimen-transport modules, (e.g., stations 52 and 54 in FIG. 6) and along path F, shown in FIG. 6, to a similar "spanning" position on the opposite side of the module. Having reached this second position, the so-transported rack will be acted upon by the X/Y drive mechanism, or the redundant drive mechanism, of the adjacent module. In advancing a rack along path F, foot portion 290A of plate 290 enters one of the rack pockets (the more inboard pocket) in the manner described above. As belt 297 is driven in the X-direction, plate 290 will be slidably driven along the spline shaft 281, and the lateral surface of foot portion 290A will exert a driving force on the end wall of the rack pocket, causing the rack to be pulled along surface S and move along path F. When plate 290 reaches the end of its travel at the opposite side of the module, the specimen-container rack will be located such that the leading edge of the rack will only have reached the edge of the module. At this point, the spline shaft will be rotated in the opposite direction so as to remove the foot member 290A from engagement with the rack. The belt drive 295 will operate in the reverse direction to position plate 290 behind the trailing edge of the rack. Then, the spline shaft will rotate again in the opposite direction to fully extend the foot member again, and the belt drive will again be reversed to drive the plate in the forward direction along the spline shaft. In doing so, the extended foot portion will drivingly engage the rear edge of the rack and thereby act to push the rack until the rack has advanced to the module-spanning position shown in FIGS. 6 and 23, this time on the opposite side of the module. The rack is then in a position to be advanced further by the adjacent module in the manner described above. Being able to bypass a module of a multi-instrument workcell in the manner described allows the workcell instruments to remain connected, even when one of the transport modules of an instrument experiences a failure of either one of its rack-transport systems. This redundancy of the rack drive adds to the overall availability of the workcell, and it reduces the level of operator intervention.

The invention has been described with reference to certain preferred embodiments. Clearly, variations can be made without departing from the spirit of the invention, and such variations are intended to fall within the scope of the appended claims.

What is claimed is:

1. A specimen transport system (MOD 22) for use with an automated clinical instrument (12) for transporting racks (R) supporting a plurality of specimen containers (C), in a linear array, atop a rack-supporting surface (S) relative to a specimen-processing apparatus (PA) of such automated clinical instrument, such specimen-processing apparatus (PA) serving to extract a desired volume of specimen from a specimen container (C) presented thereto for analysis by such automated clinical instrument, said specimen transport system (MOD 22) comprising:
   a housing (H) containing:
   (a) an input station (40) that is configured to receive one or more racks of specimen containers;
   (b) a specimen-processing station (50) at which individual racks of specimen containers are positioned to present a volume of specimen for extraction by the specimen processing apparatus of such automated clinical instrument;
   (c) an output station (42) that is configured to receive one or more racks of specimen containers after a contained portion of a specimen has been extracted from at least one container in said rack; and
   (d) a rack-transporting mechanism (70) configured to selectively transport each rack of specimen containers in the input station, one at a time, and independent of the transport of other racks containing said specimen containers, along any one of the following paths:
   (i) a path leading away from said input station and leading to said specimen-processing station,
   (ii) a path leading away from said specimen-processing station and leading to said output station, and
   (iii) a reflex path leading away from said specimen-processing station and returning back to said specimen-processing station to enable a reflex analysis of a previously analyzed specimen by said clinical instrument, said rack-transport mechanism being further configured to selectively transport the rack, along the bottom edge of the rack, back towards said specimen-processing station along the same path the rack was previously transported away from said specimen-processing station, and wherein said specimen processing station is located within said housing between said input station and said output station.

2. The specimen transport system as defined by claim 1 wherein said rack-transporting mechanism operates to transport said racks as defined in sub-paragraphs (i)-(iii) over a plane and featureless surface.

3. The specimen transport system as defined by claim 2 wherein said rack-transporting mechanism comprises an X/Y drive mechanism that-drivingly engages racks via magnetic forces to transport said racks in mutually perpendicular directions over said plane and featureless surface.

4. The specimen transport system as defined by claim 1 wherein said specimen-transport system is further constructed to deliver a rack of specimen containers into contact with an external transport system that is located adjacent to said specimen transport system, and to cooperate with such external transport system to transfer a rack of specimen containers thereto.

5. The specimen transport system as defined by claim 1 wherein said rack-transporting mechanism comprises a bi-directional motor for advancing said racks in opposite directions along said paths.

* * * * *